(12) United States Patent (10) Patent No.: US 9,125,414 B2
Le Vezouet et al. (45) Date of Patent: Sep. 8, 2015

(54) PYRIDINE DERIVATIVES COMPOUNDS FOR CONTROLLING INVERTEBRATE PESTS

(75) Inventors: Ronan Le Vezouet, Mannheim (DE); Sebastian Soergel, Ludwigshafen (DE); Christian Defieber, Mannheim (DE); Steffen Gross, Ludwigshafen (DE); Karsten Koerber, Eppelheim (DE); Deborah L. Culbertson, Fuquay Varina, NC (US); Douglas D. Anspaugh, Apex, NC (US)

(73) Assignee: BASF SE, Ludwigshafen (DE)

( * ) Notice: Subject to any disclaimer, the term of this patent is extended or adjusted under 35 U.S.C. 154(b) by 79 days.

(21) Appl. No.: 13/386,473

(22) PCT Filed: Jul. 15, 2010

(86) PCT No.: PCT/EP2010/060243
§ 371 (c)(1),
(2), (4) Date: Jan. 23, 2012

(87) PCT Pub. No.: WO2011/009804
PCT Pub. Date: Jan. 27, 2011

(65) Prior Publication Data
US 2012/0122681 A1 May 17, 2012

Related U.S. Application Data

(60) Provisional application No. 61/228,205, filed on Jul. 24, 2009.

(51) Int. Cl.
*A01N 43/40* (2006.01)
*A01P 7/04* (2006.01)
(Continued)

(52) U.S. Cl.
CPC .............. *A01N 43/80* (2013.01); *A01N 43/50* (2013.01); *A01N 43/76* (2013.01); *A01N 43/78* (2013.01); *C07D 401/12* (2013.01); *C07D 413/12* (2013.01); *C07D 417/12* (2013.01)

(58) Field of Classification Search
CPC ....... A01N 43/80; A01N 43/78; A01N 43/50; A01N 43/76; C07D 413/12; C07D 417/12; C07D 401/12
See application file for complete search history.

(56) References Cited

U.S. PATENT DOCUMENTS 5,360,799 A 11/1994 Bachy et al.
6,747,041 B1 6/2004 Katsuhira et al.
(Continued)

FOREIGN PATENT DOCUMENTS

CA 2 026 131 3/1991
CN 1711255 12/2005
(Continued)

OTHER PUBLICATIONS

U.S. Environmental Protection Agency, "Insect Repellents: Use and Effectiveness", <http://cfpub.epa.gov/oppref/insect/>, Updated Apr. 10, 2013, p. 1-2.*
Merriam-Webster, "Pest", <http://www.merriam-webster.com/dictionary/pest>, © 2013, p. 1-4.*
National Wildlife Federation, "Invertebrates", <http://www.nwf.org/wildlife/wildlife-library/invertebrates.aspx>, © 1996-2012, p. 1-2.*
Pest Control Methods, "Pest control methods: Natural vs. Chemical", <http://www.pestcontrolmethods.org/>, © 2012, p. 1-4.*
Britannica Online Encyclopedia, "Arthropod", <http://www.britannica.com/EBchecked/topic/36943/arthropod>, 2013, p. 1-5.*
Texas A&M Agrilife Extension, "Order Homoptera", <https://insects.tamu.edu/fieldguide/orders/homoptera.html>, 1999, p. 1.*
(Continued)

*Primary Examiner* — Tracy Vivlemore
*Assistant Examiner* — Monica Shin
(74) *Attorney, Agent, or Firm* — Brinks Gilson & Lione

(57) ABSTRACT

The present invention relates to methods and uses of compounds of formulae I or II and the salts and N-oxides thereof,

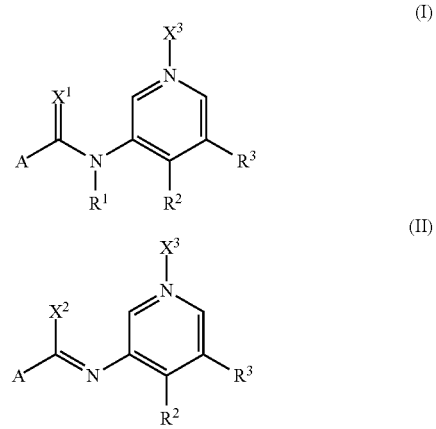

wherein
A is a substituted or unsubstituted 5-membered heterocyclic radical;
$X^1$ is S, O or $NR^{1a}$, wherein $R^{1a}$ is selected from H, $C_1$-$C_{10}$-alkyl and the like; $X^2$ is $OR^{2a}$, $NR^{2b}R^{2c}$, $S(O)_m R^{2d}$; $X^2$ is $OR^{2a}$, $NR^{2b}R^{2c}$, $S(O)_m R^{2d}$, wherein m is 0, 1 or 2, $R^{2a}$ is $C_1$-$C_4$-alkyl, $C_1$-$C_4$-haloalkyl and the like, $R^{2b}$, $R^{2c}$ are H, $C_1$-$C_4$-alkyl, $C_1$-$C_4$-haloalkyl and the like; $X^3$ is a lone pair or oxygen; $R^1$, $R^2$ and $R^3$ are, inter alia, hydrogen, and $R^1$ is H, $C_1$-$C_{10}$-alkyl and the like. The present invention further relates to a method for controlling invertebrate pests, to a method for protecting plant propagation material and/or the plants which grow therefrom, to plant propagation material, comprising at least one compound according to the present invention, to a method for treating or protecting an animal from infestation or infection by parasites and to an agricultural composition containing at least one compound according to the present invention.

4 Claims, No Drawings

(51) Int. Cl.
*A01N 43/80* (2006.01)
*A01N 43/50* (2006.01)
*A01N 43/76* (2006.01)
*A01N 43/78* (2006.01)
*C07D 401/12* (2006.01)
*C07D 413/12* (2006.01)
*C07D 417/12* (2006.01)

(56) References Cited

U.S. PATENT DOCUMENTS

| | | |
|---|---|---|
| 2006/0069132 A1 | 3/2006 | Armel et al. |
| 2007/0203148 A1 | 8/2007 | Dunkel et al. |
| 2007/0275980 A1 | 11/2007 | Yoshida et al. |
| 2008/0033513 A1 | 2/2008 | Man et al. |
| 2008/0058389 A1 | 3/2008 | Dunkel et al. |
| 2009/0163516 A1 | 6/2009 | Dunkel et al. |
| 2009/0176844 A1 | 7/2009 | Dunkel et al. |
| 2009/0247586 A1 | 10/2009 | Dunkel et al. |
| 2009/0286800 A1 | 11/2009 | Cheruvallath et al. |

FOREIGN PATENT DOCUMENTS

| | | |
|---|---|---|
| CN | 1927838 | 3/2007 |
| CN | 101062916 | 10/2007 |
| CN | 101062919 | 10/2007 |
| EP | 0 419 944 | 4/1991 |
| EP | 0573883 | 12/1993 |
| EP | 0606175 | 7/1994 |
| EP | 0 891 975 | 1/1999 |
| EP | 1 188 745 | 3/2002 |
| EP | 2 263 455 | 12/2010 |
| JP | 10195072 | 7/1998 |
| JP | 2001159610 | 6/2001 |
| JP | 2001348378 | 12/2001 |
| JP | 2004-269515 | 9/2004 |
| JP | 2004331541 | 11/2004 |
| JP | 2005-532367 | 10/2005 |
| JP | 2006/520373 | 9/2006 |
| JP | 2007/77106 | 3/2007 |
| JP | 2008-285482 | 11/2008 |
| WO | WO 98/54154 | 12/1998 |
| WO | WO 99/48868 | 9/1999 |
| WO | WO 00/29398 | 5/2000 |
| WO | WO 01/00575 | 1/2001 |
| WO | WO 02/070483 | 9/2002 |
| WO | WO 02/094791 | 11/2002 |
| WO | WO 03/037900 | 5/2003 |
| WO | WO 03/106427 | 12/2003 |
| WO | WO 2004/017908 | 3/2004 |
| WO | WO 2004/035545 | 4/2004 |
| WO | WO 2004/046129 | 6/2004 |
| WO | WO 2004/076458 | 9/2004 |
| WO | WO 2004/080999 | 9/2004 |
| WO | WO 2004/106324 | 12/2004 |
| WO | WO 2005/040152 | 5/2005 |
| WO | WO 2005/073165 | 5/2005 |
| WO | WO 2005/074686 | 8/2005 |
| WO | WO 2005/075411 | 8/2005 |
| WO | WO 2006/015860 | 2/2006 |
| WO | WO 2006/045522 | 5/2006 |
| WO | WO 2006/074445 | 7/2006 |
| WO | WO 2006/133926 | 12/2006 |
| WO | WO 2007/046548 | 4/2007 |
| WO | WO 2007/046550 | 4/2007 |
| WO | WO 2007/065664 | 6/2007 |
| WO | WO 2007/068373 | 6/2007 |
| WO | WO 2007/068375 | 6/2007 |
| WO | WO 2007/068377 | 6/2007 |
| WO | WO 2007/085188 | 8/2007 |
| WO | WO 2007/121687 | 11/2007 |
| WO | WO 2007/139856 | 12/2007 |
| WO | WO 2007/139860 | 12/2007 |
| WO | WO 2008/116898 | 10/2008 |
| WO | WO 2009/027393 | 3/2009 |
| WO | WO 2009/086303 | 7/2009 |
| WO | WO 2010/017047 | 2/2010 |
| WO | WO 2010/023277 | 3/2010 |
| WO | WO 2010/034737 | 4/2010 |
| WO | WO 2010/034738 | 4/2010 |
| WO | WO 2011/003793 | 1/2011 |
| WO | WO 2011/003796 | 1/2011 |

OTHER PUBLICATIONS

Cranshaw et al., "Spider Mites", Colorado State University Extension, Fact Sheet No. 5.507, Insect Series: Home and Garden, Nov. 2006, p. 1-3.*

Technicide, "Pest Control", <http://technicide.com/Pest-Control>, © 2006, p. 1-2.*

Buzzle, "Wast Insect Control: Wasp Traps and Repellent", <http://www.buzzle.com/articles/wasp-insect-control-wasp-traps-andrepellent.html>, Dec. 8, 2007, p. 1-2.*

Shelton et al., "Effects of Weeds on the Diversity and Abundance of Insects in Soybeans," Environmental Entomology, vol. 12, No. 2, Apr. 1983, p. 296-298.*

Bayhan et al., "Effect of temperature on development, mortality, fecundity, and reproduction of *Aphis rumicis* L. (Homoptera: Aphididae) on broadleaf dock (*Rumex obtusifolius*) and Swiss chard (*Beta vulgaris* vulgaris var. cida)," J Pest Sci (2006) 79: 57-61.*

International Preliminary Report on Patentability issued Jan. 24, 2012, from corresponding International Application No. PCT/EP2010/060243, filed Jul. 15, 2010.

International Search Report completed Mar. 18, 2011, in International Application No. PCT/EP2010/060243, filed Jul. 1, 2010.

Milyutin, A.V., et al. "Synthesis properties and biological activity of 3-pyridylamides of 4-aryl-2-hydroxy-4-oxo-2-butenic (Aroylpyruvic) acids", Pharmaceutical Chemistry Journal, 1997, p. 30-33, vol. 31, No. 1.

Persson, Tobias, et al., "Pyrazole carboxamides and carboxylic acids as protein kinase inhibitors in aberrant eukaryotic signal transduction: induction of growth arrest in MCF-7 cancer cells", Organic & Biomolecular Chemistry, 2007, pp. 3963-3970, vol. 5.

Sharlow et al., "Development and Implementation of a Miniaturized High-Throughput Time-Resolved Fluorescence Energy Transfer Assay to Identify Small Molecule Inhibitors of Polo-Like Kinase 1," ASSAY and Drug Development Technologies, vol. 5, No. 6, (2007), pp. 723-735.

Office Action dated Oct. 11, 2013, from U.S. Appl. No. 13/382,225, filed Jan. 4, 2012.

Office Action dated May 21, 2013, from U.S. Appl. No. 13/382,229.

Office Action dated Feb. 25, 2014, from U.S. Appl. No. 13/382,225, filed Jan. 4, 2012.

* cited by examiner

PYRIDINE DERIVATIVES COMPOUNDS FOR CONTROLLING INVERTEBRATE PESTS

This application is a National Stage application of International Application No. PCT/EP2010/060243 filed Jul. 15, 2010, which claims the benefit of U.S. Provisional Application No. 61/228,205 filed Jul. 24, 2009, the entire contents of which are hereby incorporated herein by reference.

The present invention relates to pyridine compounds which can be used for combating and/or controlling invertebrate pests, in particular arthropod pests. The invention also relates to a method for controlling invertebrate pests by using these compounds. The present invention also relates to seed and to an agricultural and veterinary composition comprising said compounds.

BACKGROUND OF INVENTION

Invertebrate pests and in particular arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

JP 2001-348378 describes methylisoxazoles-4-carboxilic acid derivatives and their use as pest controlling agent for agriculture and horticulture is mentioned.

EP 0573883 describes isoxazoles derivatives and their veterinary and medical use.

WO 2000/29398 describes isothiazoles-carboxylic acid derivatives and their use as biocide is mentioned.

JP 2001-159610 describes isoxazoles carboxylic acids derivatives and their use as plant disease controlling agent is mentioned.

CN 1927838 describes aromatic and heteroaromatic N-pyridinylcarboxamides useful as agrochemical bactericides and fungicides.

It is an object of the present invention to provide compounds that have a good pesticidal activity, in particular insecticidal activity, and show a broad activity spectrum against a large number of different invertebrate pests, especially against difficult to control insects.

It has been found that these objectives can be achieved by compounds of the formulae I and II below and by their salts, in particular their agriculturally or veterinarily acceptable salts.

In a first aspect the present invention relates the use controlling invertebrate pests which method comprises treating the pests, their food supply, their habitat or their breeding ground or a plant, seed, soil, area, material or environment in which the pests are growing or may grow, or the materials, plants, seeds, soils, surfaces or spaces to be protected from pest attack or infestation with a pesticidally effective amount of a compound of the formulae I or II or a salt or N-oxide thereof:

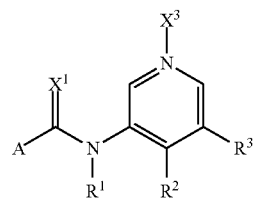
(I)

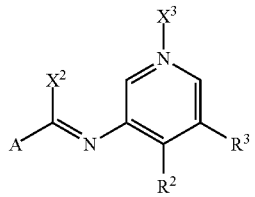
(II)

wherein

A is an oxazole or thiazole or imidazole or isoxazole or isothiazole radical of the formulae A1a, A1, A2a, A2, A3a, A3

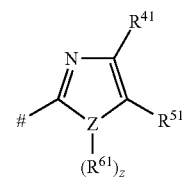
A1

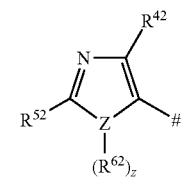
A2

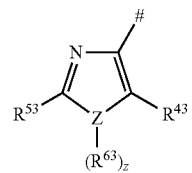
A3

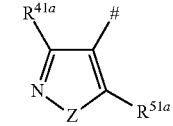
A1a

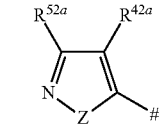
A2a

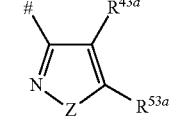
A3a

\# denotes the binding site to the remainder of formulae I or II;

$X^3$ is a lone pair or oxygen;

Z is O or S if z=0 or

Z is N if z=1

$R^1$ is hydrogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $OR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, phenyl, hetaryl, heterocyclyl, $C_1$-$C_5$-alkylen-$OR^a$, $C_1$-$C_5$-alkylen-CN, phenyl-$C_1$-$C_5$-alkyl, hetaryl-$C_1$-$C_5$-alkyl, heterocyclyl-$C_1$-$C_5$-alkyl, $C_3$-$C_{10}$-cycloalkyl-$C_1$-$C_5$-alkyl, $C_1$-$C_5$-alkylen-$C(Y)R^b$, —$C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_2R^d$, $C_1$-$C_5$-alkylen-$S(O)_mNR^eR^d$, $C_1$-$C_5$-alkylen-$C(Y)NR^iNR^eR^f$ wherein the last sixteen mentioned radicals may be unsubstituted or may carry 1, 2, 3, 4 or 5 identical or different substituents $R^x$ or $R^y$ and wherein m is 0, 1 or 2;

$R^2$ is hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$R^3$ is hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$R^{41}$, $R^{41a}$, $R^{42}$, $R^{43}$, $R^{43a}$, $R^{51}$, $R^{51a}$, $R^{52}$, $R^{52a}$, $R^{53}$ and $R^{53a}$ are independently selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $C(Y)R^b$, $C(Y)OR^c$, $S(O)_mR^d$, $NR^eR^f$, $C(Y)NR^gR^h$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$, with the proviso that either $R^{41a}$ or $R^{51a}$ is H if Z is O;

$R^{42a}$ is selected from the group consisting of hydrogen, halogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $C(Y)R^b$, $C(Y)OR^c$, $S(O)_mR^d$, $NR^eR^f$, $C(Y)NR^gR^h$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$;

$R^{61}$, $R^{62}$, $R^{63}$ are selected from the group consisting of hydrogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $C(Y)R^b$, $C(Y)OR^c$, $S(O)_mR^d$, $NR^eR^f$, $C(Y)NR^gR^h$, $S(O)_mNR^eR^f$, $C(Y)NR^iNR^eR^f$, heterocyclyl, heterocyclyl-$C_1$-$C_5$-alkyl, heteroaryl, heteroaryl-$C_1$-$C_5$-alkyl, $C_3$-$C_{10}$-cycloalkyl, $C_3$-$C_{10}$-cycloalkyl-$C_1$-$C_5$-alkyl, cycloalkenyl, $C_5$-$C_{10}$-cycloalkenyl-$C_1$-$C_5$-alkyl, phenyl, phenyl-$C_1$-$C_5$-alkyl, $C_1$-$C_5$-alkylen-ORB, $C_1$-$C_5$-alkylen-CN, $C_1$-$C_5$-alkylen-$C(Y)R^b$, $C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_mR^d$, $C_1$-$C_5$-alkylen-$S(O)_mNR^eR^f$, $C_1$-$C_5$-alkylen-$C(Y)NR^iNR^eR^f$, wherein the last nineteen mentioned radicals may be unsubstituted or may carry 1, 2, 3, 4 or 5 identical or different substituents $R^x$ or $R^y$ and wherein m is 0, 1 or 2;

Y is O or S;

$X^1$ is S, O or $NR^{1a}$, wherein $R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, heterocyclyl, phenyl-$C_1$-$C_4$-alkyl, hetaryl-$C_1$-$C_4$-alkyl, heterocyclyl-$C_1$-$C_4$-alkyl wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^2$ is $OR^{2a}$, $NR^{2b}R^{2c}$, $S(O)_mR^{2d}$, wherein m is 0, 1 or 2, wherein $R^{2a}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2b}$, $R^{2c}$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2d}$ is selected from $C_1$-$C_4$-alkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; $R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or substituents which are independently of each other selected from halogen, cyano, nitro, $C_1$-$C_4$-alkyl, $C_1$-$C_4$-alkoxy and $C_1$-$C_4$-haloalkoxy;

$R^i$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals $R^y$; and wherein $R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl wherein m is 0, 1 or 2 and $R^d$ as above defined.

In a second aspect, the present invention provides a method for controlling invertebrate pests which method comprises treating the pests, their food supply, their habitat or their breeding ground or a plant, plant propagation material (such as seed), soil, area, material or environment in which the pests are growing or may grow, or the materials, plants, plant propagation materials (such as seeds), soils, surfaces or spaces to be protected from pest attack or infestation with a pesticidally effective amount of a compound of the formulae I or II or a salt or N-oxide thereof or with a pesticidally effective amount of an agricultural composition containing at least one compound of the formulae I or II or a salt or N-oxide thereof.

In a third aspect, the present invention provides a method for protecting seed and/or the plants which grow therefrom, against infestation by invertebrate pests, which method comprises treating the seed with a pesticidally effective amount of a compound of the formulae I or II or an agriculturally acceptable salt or N-oxide thereof. A further object of the present invention is seed, comprising at least one compound of formulae I or II and/or an agriculturally acceptable salt or N-oxide thereof.

The invention further provides a method for treating or protecting an animal from infestation or infection by parasites, especially ectoparasites, which method comprises bringing the animal in contact with a parasiticidally effective amount of a compound of the formulae I or II or a veterinally acceptable salt or N-oxide thereof as defined above. Bringing the animal in contact with the compound I or II, its salt or the veterinary composition of the invention means applying or administering it to the animal.

Therefore, the compounds of the formulae I and II and their salts, in particular their agriculturally or veterinarily acceptable salts, and their N-oxides are also part of the invention.

Another object of the present invention is an agricultural composition containing at least one compound of the formulae I or II as defined above and/or an agriculturally acceptable salt or an N-oxide thereof and at least one liquid or solid carrier.

Another object of the present invention is a veterinary composition containing at least one compound of the formulae I or II as defined above and/or a veterinarily acceptable salt or an N-oxide thereof and at least one veterinarily acceptable liquid or solid carrier.

The present invention further relates to plant propagation material, such as seed, comprising at least one compound of formulae I or II as defined herein.

The present invention further relates to the uses of compounds of formulae I or II as defined herein for controlling invertebrate pests.

In the compounds of formulae I or II the substituents on A or the pyridyl ring may contain one or more centers of chirality. In this case the compounds of the formulae I or II can be present in the form of different enantiomers or diastereomers, depending on the substituents. In case of the formula II, the compound II may also exist as a cis- or trans-isomer with respect to the N=C axis. The present invention relates to every possible stereoisomer of the compounds of general formulae I or II, i.e. to single enantiomers or diastereomers, as well as to mixtures thereof.

The compounds of formulae I or II may be amorphous or may exist in one or more different crystalline states (polymorphs) which may have a different macroscopic properties such as stability or show different biological properties such as activities.

The present invention includes both amorphous and crystalline compounds of formulae I or II, mixtures of different crystalline states of the respective compound I or II, as well as amorphous or crystalline salts thereof.

Salts of the compounds of the formulae I or II are preferably agriculturally and veterinarily acceptable salts. They can be formed in a customary method, e.g. by reacting the compound with an acid of the anion in question if the compound of formula I has a basic functionality or by reacting an acidic compound of formulae I or II with a suitable base.

Agriculturally useful salts of the compounds I and II encompass especially the salts of those cations or the acid addition salts of those acids whose cations and anions, respectively, have no adverse effect on the pesticidal action of the compounds I or II. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen-sulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formulae (I) and (II) with an acid of the corresponding anion, preferably of hydrochloric acid, hydrobromic acid, sulfuric acid, phosphoric acid or nitric acid.

Veterinarily acceptable salts of the compounds of formula (I) encompass especially the salts of those cations or the acid addition salts which are known and accepted in the art for the formation of salts for veterinary use. Suitable acid addition salts, e.g. formed by compounds of formulae I or II containing a basic nitrogen atom, e.g. an amino group, include salts with inorganic acids, for example hydrochlorids, sulphates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The term "N-oxide" includes any compound of the formulae I or II which, apart from the pyridine nitrogen that carries the moiety $X^3$, has at least one tertiary nitrogen atom that is oxidized to an N-oxide moiety.

The term "invertebrate pest" as used herein encompasses animal populations, such as insects, arachnids and nematodes, which may attack plants thereby causing substantial damage to the plants attacked, as well as ectoparasites which may infest animals, e.g. mammals, birds or fish, thereby causing damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35, Curr. Opin. Chem. Biol. 2006 October; 10(5): 487-91. Epub 2006 Aug. 28, Biomaterials. 2001 March; 22(5):405-17, Bioconjug Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from *bacillus thuringiensis*, such as ä-endotoxins, a g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora* infestans derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxyalkyl, alkylamino, dialkylamino, alkylcarbonyl, alkylthio, alkylsulfinyl and alkylsulfonyl denotes in each case a straight-chain or branched alkyl group having usually from 1 to 10 carbon atoms, frequently from 1 to 6 carbon atoms, preferably 1 to 4 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-oxtyl, 1-methyloctyl, 2-methylheptyl, 1-ethylhexyl, 2-ethylhexyl, 1,2-dimethylhexyl, 1-propylpentyl and 2-propylpentyl.

The term "haloalkyl" as used herein and in the haloalkyl moieties of haloalkylthio and haloalkylsulfonyl, denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl such as fluoromethyl, difluoro-methyl, trifluoromethyl, 1-fluoroethyl, 2-fluoroethyl, 2,2-difluoroethyl, 2,2,2-trifluoroethyl, pentafluoroethyl, heptafluoroisopropyl and the like.

The term "alkoxy" as used herein denotes in each case a straight-chain or branched alkyl group which is bound via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2- dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylpentyloxy, n-oxtyloxy, 1-methyloctyloxy, 2-methylheptyloxy, 1-ethylhexyloxy, 2-ethylhexyloxy, 1,2-dimethylhexyloxy, 1-propylpentoxy and 2-propylpentyloxy.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluoroethoxy, 2,2,2-trichloroethoxy, pentafluoroethoxy and the like.

The term "cycloalkyl" as used herein and in the cycloalkyl moieties of $C_3$-$C_{10}$-cycloalkylmethyl denotes in each case a mono- or bicyclic cycloaliphatic radical having usually from 3 to 10 C atoms or 3 to 6 C atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "halocycloalkyl" as used herein and in the halocycloalkyl moieties of $C_3$-$C_{10}$-halocycloalkyl-methyl denotes in each case a mono- or bicyclic cycloaliphatic radical having usually from 3 to 10 C atoms or 3 to 6 C atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclopropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "alkenyl" as used herein denotes in each case a singly unsaturated hydrocarbon radical having usually 2 to 10, e.g. 2, 3, 4, 5, 6, 7 or 8 C-atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 10, e.g. 2, 3, 4, 5, 6, 7 or 8 C-atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "$C_1$-$C_4$-alkoxy-$C_1$-$C_4$-alkyl" as used herein refers to $C_1$-$C_4$-alkyl wherein 1 carbon atom carries a $C_1$-$C_4$-alkoxy radical as mentioned above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkylthio "(alkylsulfanyl: alkyl-S—)" as used herein refers to a straight-chain or branched saturated alkyl group having 1 to 10 carbon atoms, preferably 1 to 4 carbon atoms (=$C_1$-$C_4$-alkylthio) (as mentioned above) which is attached via a sulfur atom.

The term "haloalkylthio" as used herein refers to a alkylthio group as mentioned above wherein the hydrogen atoms are partially or fully substituted by fluorine, chlorine, bromine and/or iodine.

The term "alkylsulfinyl" (alkylsulfoxyl: $C_1$-$C_6$-alkyl-S(=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl) bonded through the sulfur atom of the sulfinyl group at any position in the alkyl group.

The term "haloalkylsulfinyl" as used herein refers to a alkylsulfinyl group as mentioned above wherein the hydrogen atoms are partially or fully substituted by fluorine, chlorine, bromine and/or iodine.

The term "alkylsulfonyl" (alkyl-S(=O)$_2$—) as used herein refers to a straight-chain or branched saturated alkyl group having 1 to 10 carbon atoms, preferably 1 to 4 carbon atoms (=$C_1$-$C_4$-alkylsulfonyl) (as mentioned above) which is bonded via the sulfur atom of the sulfonyl group at any position in the alkyl group.

The term "haloalkylsulfonyl" as used herein refers to a alkylsulfonyl group as mentioned above wherein the hydrogen atoms are partially or fully substituted by fluorine, chlorine, bromine and/or iodine.

The term "heterocyclyl" includes in general 5-, 6-, 7- or 8-membered monoheterocyclic radicals and 8 to 10 membered bicyclic heterocyclic radicals, the mono- and bicyclic radicals may be saturated, unsaturated or aromatic (=hetaryl). The mono- and bicyclic heterocyclic radicals as usually comprise 1, 2, 3 or 4 heteroatoms selected from N, O and S as ring members.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2, 4-triazolyl and tetrazolyl, i.e. 1H- or 2H-tetrazolyl.

The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

Examples of saturated or unsaturated membered heterocyclic rings comprise saturated or unsaturated, non-aromatic heterocyclic rings, such as pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, dihydrothiopyranyl, tetrahydrothiopyranyl, morpholinyl, thiazinyl and the like. Examples for heterocyclic ring also comprising 1 or 2 carbonyl groups as ring members comprise pyrrolidin-2-only, pyrrolidin-2,5-dionyl, imidazolidin-2-only, oxazolidin-2-only, thiazolidin-2-only and the like.

The terms "phenyl-$C_1$-$C_4$-alkyl" and "phenoxy-$C_1$-$C_4$-alkyl" refers to phenyl or phenoxy, respectively, which are bound via a $C_1$-$C_4$-alkyl group, in particular a methyl group (=hetarylmethyl), to the remainder of the molecule, examples including benzyl, 1-phenylethyl, 2-phenylethyl, 2-phenoxyethyl etc.

The terms "heterocyclyl-$C_1$-$C_4$-alkyl" and "hetaryl-$C_1$-$C_4$-alkyl" refers to heterocyclyl or hetaryl, respectively, as defined above which are bound via a $C_1$-$C_4$-alkyl group, in particular a methyl group (=heterocyclylmethyl or hetarylmethyl, respectively), to the remainder of the molecule.

The remarks made below as to preferred embodiments of the variables of the compounds of the formulae I or II, of the features of the use and method according to the invention and of the composition of the invention are valid on their own as well as—preferably—in combination with each other.

A preferred embodiment of the invention relates to the method and uses of pyridine compounds of the formula I, to their salts, to their N-oxides. Amongst the compounds of the formula I, preference is given to those compounds, wherein $X^1$ in formula I is oxygen, sulphur or a moiety N—$R^{1a}$.

Particular preference is given to the methods and uses of those compounds of the formula I wherein $X^1$ is oxygen.

In the methods and uses of compounds of the formula I, wherein $X^1$ is $NR^{1a}$, a particular embodiment relates to the uses of those compounds, wherein $R^{1a}$ is $C_1$-$C_6$-alkyl, $C_1$-$C_6$-haloalkyl, $C_3$-$C_6$-cycloalkyl, $C_3$-$C_6$-cycloalkylmethyl, $C_3$-$C_6$-halocycloalkyl, $C_2$-$C_6$-alkenyl, $C_2$-$C_6$-haloalkenyl, $C_2$-$C_6$-alkynyl, $C_1$-$C_4$-alkoxy-$C_1$-$C_6$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, or a moiety ORB. In particular, $R^{1a}$ is $C_1$-$C_6$-alkyl, $C_3$-$C_6$-cycloalkylmethyl, $C_3$-$C_6$-alkenyl, $C_3$-$C_6$-alkynyl, $C_1$-$C_4$-alkoxy-$C_1$-$C_4$-alkyl or a moiety ORB, wherein $R^a$ is as defined above and in particular selected from $C_1$-$C_6$-alkyl, $C_3$-$C_6$-cycloalkylmethyl, $C_3$-$C_6$-alkenyl, $C_3$-$C_6$-alkynyl and $C_1$-$C_4$-alkoxy-$C_1$-$C_4$-alkyl.

Amongst the methods and uses of compounds of the formula I, preference is given to the uses of those compounds, wherein $R^1$ is hydrogen, CN, $C_1$-$C_{10}$-alkyl, $C_2$-$C_{10}$-alkenyl, $C_2$-$C_{10}$-haloalkenyl, $C_2$-$C_{10}$-alkynyl, $C_1$-$C_4$-alkoxy-$C_1$-$C_{10}$-alkyl, $C_1$-$C_4$-alkylene-CN, $OR^a$, $C(Y)R^b$, $C(Y)ORG$ or $S(O)_2R^d$. More preference is given to the use of compounds of formula I, wherein $R^1$ is hydrogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_4$-alkoxy-$C_1$-$C_{10}$-alkyl or $C_1$-$C_4$-alkylene-CN, in particular hydrogen, $C_1$-$C_3$-alkyl or $C_1$-$C_4$-alkylene-CN, in particular hydrogen, methyl or ethyl.

Another embodiment of the invention relates to the methods and uses of compounds of the formula II, to their salts, to their N-oxides. In the compounds of the formula II, preference is given to the uses of those compounds, wherein $X^2$ in formula II is $OR^{2a}$ or $SR^{2a}$. In these compounds $R^{2a}$ is preferably $C_1$-$C_6$-alkyl, $C_3$-$C_6$-alkenyl, $C_3$-$C_6$-alkynyl, $C_3$-$C_6$-cycloalkylmethyl or $C_1$-$C_4$-alkoxy-$C_1$-$C_{10}$-alkyl. Another embodiment relates to the methods and uses of compounds of the formula II, wherein $X^2$ is $NR^{2b}R^{2c}$. In these compounds $R^{2b}$ and $R^e$ are preferably selected, independently of each other, from $C_1$-$C_6$-alkyl, $C_3$-$C_6$-cycloalkylmethyl or $C_1$-$C_4$-alkoxy-$C_1$-$C_{10}$-alkyl or $R^{2b}$ and $R^{2c}$, together with the nitrogen atom to which they are attached, form a saturated, nitrogen-bound 5- or 6-membered heterocycle which may comprise a further heteroatom selected from O, S and N, e.g. $NR^{2b}R^{2c}$ being 1-pyrrolidinyl, 1-piperidinyl, 1-piperazinyl, 4-morpholinyl or 4-thiomorpholinyl.

In the methods and uses of the compounds according to the present invention, preference is given to the methods and uses of compounds wherein $R^2$ in formulae I and II is selected from hydrogen, methyl, difluoromethyl, trifluoromethyl, methoxy, difluoromethoxy and trifluoromethoxy.

In the methods and uses of the compounds according to the present invention, preference is given to the methods and uses of compounds, wherein $R^3$ in formulae I and II is selected from hydrogen, methyl, difluoromethyl, trifluoromethyl, methoxy, difluoromethoxy and trifluoromethoxy.

In particular, at least one of the radicals $R^2$ or $R^3$ in formulae I and II is hydrogen. A very preferred embodiment of the invention relates to the methods and uses of compounds of the formulae I and II and to their salts, wherein both $R^2$ and $R^3$ are hydrogen.

Another preferred embodiment of the invention relates to the methods and uses of compounds of the formulae I and II and to their salts and to their N-oxides, wherein $R^2$ is hydrogen and $R^3$ is selected from hydrogen, methyl, difluoromethyl, trifluoromethyl, methoxy, difluoromethoxy and trifluoromethoxy. Another preferred embodiment of the invention relates to the methods and uses of compounds of the formulae I and II and to their salts, wherein $R^3$ is hydrogen and $R^2$ is selected from hydrogen, methyl, difluoro-methyl, trifluoromethyl, methoxy, difluoromethoxy and trifluoromethoxy.

A preferred embodiment of the invention relates to the methods and uses of compounds of the formulae I and II, to their salts, to their N-oxides, wherein A is a radical A1a. Amongst these, preference is given to the methods and uses of such preferred compounds of formula I, wherein $X^1$, $R^1$, $R^2$ and $R^3$ are as defined above and in particular have one of the preferred meanings.

Preference is given to the methods and uses of such preferred compounds of formula I and II, wherein A is a radical A1a, Z is O, either $R^{41a}$ or $R^{51a}$ is hydrogen and the remaining radical is preferably selected from hydrogen, halogen, CN, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$. In particular, preference is given to the methods and uses of compounds of formulae I wherein A is a radical A1a, Z is O, either $R^{41a}$ or $R^{51a}$ is hydrogen and the remaining radical $R^{41a}$ or $R^{51a}$ is selected from hydrogen, halogen, CN, $C_1$-$C_4$-haloalkyl, $C_3$-$C_6$-cycloalkyl and $C_3$-$C_6$-halocycloalkyl. More preferably, the remaining radical $R^{41a}$ or $R^{51a}$ in A1a is selected from hydrogen, methyl, ethyl, propyl, $CHF_2$, $CF_3$, Cl, Br.

Preference is also given to the methods and uses of such preferred compounds of formula I and II, wherein A is a radical A1a, Z is S, $R^{41a}$ and $R^{51a}$ are independently from each other selected from hydrogen, halogen, CN, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$. In particular, preference is given to the methods and uses of compounds of formulae I wherein A is a radical A1a, Z is S, $R^{41a}$ and $R^{51a}$ are independently from each other selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl. More preferably $R^{41a}$ or $R^{51a}$ are selected from hydrogen, methyl, ethyl, propyl, $CHF_2$, $CF_3$, Cl, Br.

A preferred embodiment of the invention relates to the methods and uses of compounds of the formulae I and II, to their salts, to their N-oxides, wherein A is a radical A1. Amongst these, preference is given to the methods and uses of such preferred compounds of formula I, wherein $X^1$, $R^1$, $R^2$ and $R^3$ are as defined above and in particular have one of the preferred meanings.

Preferably, at least one or both of the radicals $R^{41}$ and $R^{51}$ are hydrogen. In particular, $R^{41}$ and $R^{51}$ are independently selected from halogen, CN, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$. Preferably, either $R^{41}$ or $R^{51}$ is selected from halogen, CN, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$, while the remaining radical $R^{41}$ or $R^{51}$ is hydrogen or halogen, in particular hydrogen. More preferably, $R^{41}$ and $R^{51}$ are selected from halogen, CN, $C_1$-$C_4$-haloalkyl, $C_3$-$C_6$-cycloalkyl and $C_3$-$C_6$-halocycloalkyl, and most preferably from $CH_3$, $CH_2CH_3$, $CHF_2$, $CF_3$, Cl, Br.

In the methods and uses of compounds of the formulae I and II, wherein A is a radical A1, $R^{61}$ is preferably selected from the group consisting of $C_1$-$C_{10}$-alkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{51}$ is $C_1$-$C_4$-alkyl or $C_1$-$C_4$-haloalkyl, in particular methyl, ethyl, n-propyl, isopropyl, Butyl, iso-butyl, sec-butyl, difluoromethyl, trifluoromethyl, 2-fluoroethyl, 2,2-difluoroethyl and 2,2,2-trifluoroethyl. In particular, more preferably are the methods and uses of compounds of the formulae I, wherein A is a radical A1, and $R^{61}$ is more preferably selected from hydrogen, methyl, ethyl, propyl, butyl, iso-butyl, sec-butyl, 2,2,2-trifluoroethyl.

Examples of such radicals of formula A1a or A1 are hereunder listed

Examples of suitable radicals A are the radicals numbered A1a1 to A1a63 which are radicals of the formulae A1a wherein Z is S, $R^{41a}$ and $R^{51a}$ are as defined in one row of the following Table A (radicals A1a1 to A1a63):

TABLE A

| Radical A1a | $R^{51a}$ | $R^{41a}$ |
|---|---|---|
| A1a1 | Me | H |
| A1a2 | Et | H |
| A1a3 | Pr | H |
| A1a4 | $CHF_2$ | H |
| A1a5 | $CF_3$ | H |
| A1a6 | Cl | H |
| A1a7 | Br | H |
| A1a8 | H | Me |
| A1a9 | Me | Me |
| A1a10 | Et | Me |
| A1a11 | Pr | Me |
| A1a12 | $CHF_2$ | Me |
| A1a13 | $CF_3$ | Me |
| A1a14 | Cl | Me |
| A1a15 | Br | Me |
| A1a16 | H | Et |
| A1a17 | Me | Et |
| A1a18 | Et | Et |
| A1a19 | Pr | Et |
| A1a20 | $CHF_2$ | Et |
| A1a21 | $CF_3$ | Et |
| A1a22 | Cl | Et |
| A1a23 | Br | Et |
| A1a24 | H | Pr |
| A1a25 | Me | Pr |
| A1a26 | Et | Pr |
| A1a27 | Pr | Pr |
| A1a28 | $CHF_2$ | Pr |
| A1a29 | $CF_3$ | Pr |
| A1a30 | Cl | Pr |
| A1a31 | Br | Pr |
| A1a32 | H | $CHF_2$ |
| A1a33 | Me | $CHF_2$ |
| A1a34 | Et | $CHF_2$ |
| A1a35 | Pr | $CHF_2$ |
| A1a36 | $CHF_2$ | $CHF_2$ |
| A1a37 | $CF_3$ | $CHF_2$ |
| A1a38 | Cl | $CHF_2$ |
| A1a39 | Br | $CHF_2$ |
| A1a40 | H | $CF_3$ |
| A1a41 | Me | $CF_3$ |
| A1a42 | Et | $CF_3$ |
| A1a43 | Pr | $CF_3$ |
| A1a44 | $CHF_2$ | $CF_3$ |
| A1a45 | $CF_3$ | $CF_3$ |
| A1a46 | Cl | $CF_3$ |
| A1a47 | Br | $CF_3$ |
| A1a48 | H | Cl |
| A1a49 | Me | Cl |
| A1a50 | Et | Cl |
| A1a51 | Pr | Cl |
| A1a52 | $CHF_2$ | Cl |
| A1a53 | $CF_3$ | Cl |

TABLE A-continued

| Radical A1a | $R^{51a}$ | $R^{41a}$ |
|---|---|---|
| A1a54 | Cl | Cl |
| A1a55 | Br | Cl |
| A1a56 | H | Br |
| A1a57 | Me | Br |
| A1a58 | Et | Br |
| A1a59 | Pr | Br |
| A1a60 | $CHF_2$ | Br |
| A1a61 | $CF_3$ | Br |
| A1a62 | Cl | Br |
| A1a63 | Br | Br | and wherein Me=$CH_3$; Et=$CH_2Me$; Pr=$(CH_2)_2CH_3$.

Further radicals which may be used in hereunder are as following defined:
Bu=$(CH_2)_3CH_3$; iBu=$CH_2CH(CH_3)_2$; sBu=$CHCH_3CH_2CH_3$.

Analog to the above listed Table A, further examples of suitable radicals A are the radicals of the formulae A1a numbered A1a64 to A1a78 wherein Z is O and $R^{41a}$, $R^{51a}$ for each radical have the meaning of one line in Table A, with the proviso that either $R^{41a}$ or $R^{51a}$ is hydrogen.

Analog to the above listed Table A, further examples of suitable radicals A are the radicals of the formulae A1 numbered A1b1 to A1b63 wherein Z is O and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b64 to A1b127 wherein Z is S and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b128 to A1b191 wherein Z is NH and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b192 to A1b255 wherein Z is N—$CH_s$ and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b256 to A1b319 wherein Z is N—$CH_2CH_3$ and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b320 to A1b383 wherein Z is N—Pr and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b384 to A1b447 wherein Z is N-Bu and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b448 to A1b511 wherein Z is N-iBu and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b512 to A1b575 wherein Z is N-sBu and $R^{41}$, $R^{51}$ for each radical have the meaning of one line in Table A in analogy to respectively $R^{41a}$, $R^{51a}$.

Analog to the above listed Table A, further examples of suitable radicals A are the radicals of the formulae A1 numbered A1b576 to A1b639 wherein Z is N—$CH_2CF_3$ and $R^{41}$, $R^{51}$ for each radical have the meaning of one line in Table A in analogy to respectively $R^{41a}$, $R^{51a}$.

A further embodiment of the invention relates to the methods and uses of compounds of the formulae I and II, to their salts, wherein A is a radical A2a. Amongst these, preference is given to compounds of the formula I, wherein $X^1$, $R^1$, $R^2$ and $R^3$ are as defined above and in particular have one of the preferred meanings.

In the methods and uses of compounds of the formulae I and II, wherein A is a radical A2a, $R^{42a}$ is preferably selected from the group consisting of hydrogen, halogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated or may carry 1, 2 or 3 identical or different substituents $R^y$, $OR^a$, $C(Y)R^b$, $C(Y)OR^c$, $S(O)_mR^d$, $NR^eR^f$, $C(Y)NR^gR^h$, phenyl, phenyl-$C_1$-$C_4$-alkyl, phenoxy-$C_1$-$C_4$-alkyl, 5-membered hetaryl and heterocyclyl-$C_1$-$C_4$-alkyl wherein heterocyclyl and the aromatic ring of the 5 last mentioned radicals may be unsubstituted or may carry 1, 2, 3, 4 or 5 identical or different substituents $R^x$. Most preferably, $R^{42a}$ is selected from halogen, $C_1$-$C_4$-alkyl, $C_1$-$C_4$-haloalkyl, $C_3$-$C_6$-cycloalkyl and $C_3$-$C_6$-halocycloalkyl, and most preferably from $CH_3$, $CH_2CH_3$, $CHCF_2$, $CF_3$, Cl, Br.

In the methods and uses of compounds of the formulae I and II, wherein A is a radical A2a, $R^{52a}$ is preferably selected from the group as recited hereunder for the radical $R^{52}$.

A further embodiment of the invention relates to the methods and uses of compounds of the formulae I and II, to their salts, wherein A is a radical A2. Amongst these, preference is given to compounds of the formula I, wherein $X^1$, $R^1$, $R^2$ and $R^3$ are as defined above and in particular have one of the preferred meanings.

In the methods and uses of compounds of the formulae I and II, wherein A is a radical A2, $R^{42}$ is preferably selected from hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are as defined above and which are preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. In particular, $R^{42}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl, and more preferably from and most preferably from $CH_3$, $CH_2CH_3$, $CHCF_2$, $CF_3$, Cl, Br.

In the methods and uses of compounds of the formulae I and II, wherein A is a radical A2 or A2a, $R^{52}$ or $R^{52a}$ is preferably selected from the group consisting of hydrogen, halogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{52}$ is selected from the group consisting of hydrogen, halogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl and $C_1$-$C_4$-alkoxy-$C_1$-$C_{10}$-alkyl. Most preferably $R^{52}$ or $R^{52a}$ is hydrogen, halogen, $C_1$-$C_4$-alkyl or $C_1$-$C_4$-haloalkyl, in particular methyl, ethyl, n-propyl, isopropyl, difluoromethyl, trifluoromethyl and 2,2,2-trifluoroethyl, Br, Cl.

In the methods and uses of compounds of the formulae I and II, wherein A is a radical A2, $R^{62}$ is preferably selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{1D}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl and phenoxymethyl wherein the aromatic ring of the 3 last mentioned radicals may be unsubstituted or may carry 1, 2, 3, 4 or 5 identical or different substituents $R^x$ which is as defined above and more preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{62}$ is $C_1$-$C_4$-alkyl or $C_1$-$C_4$-haloalkyl, in particular methyl, ethyl, n-propyl, isopropyl, Butyl, iso-butyl, sec-butyl, difluoromethyl, trifluoromethyl, 2-fluoroethyl, 2,2-difluoroethyl and 2,2,2-trifluoroethyl. In particular, more preferably are the methods and uses of compounds of the formulae I, wherein A is a radical A1, and $R^{62}$ is more preferably selected from hydrogen, methyl, ethyl, propyl, butyl, iso-butyl, sec-butyl, 2,2,2-trifluoroethyl.

Examples of such radicals of formula A2a or A2 are hereunder listed:

Analog to the above listed Table A, further examples of suitable radicals A are the radicals of the formulae A2a numbered A2a1 to A2a63 wherein Z is O and $R^{42a}$, $R^{52a}$ for each radical have the meaning of one line in Table A in analogy to respectively $R^{41a}$, $R^{51a}$.

Analog to the above listed Table A, further examples of suitable radicals A are the radicals of the formulae A2a numbered A2a64 to A2a127 wherein Z is S and $R^{42a}$, $R^{52a}$ for each radical have the meaning of one line in Table A in analogy to respectively $R^{41a}$, $R^{51a}$.

Analog to the above listed Table A, further examples of suitable radicals A are the radicals of the formulae A2 numbered A2b1 to A2b63 wherein Z is O and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b64 to A2b127 wherein Z is S and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b128 to A2b191 wherein Z is NH and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b192 to A2b255 wherein Z is $NCH_3$ and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b256 to A2b319 wherein Z is N-Et and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b320 to A2b383 wherein Z is N—Pr and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b384 to A2b447 wherein Z is N-Bu and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b448 to A2b511 wherein Z is N-iBu and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b512 to A2b575 wherein Z is N-sBu and $R^{42}$, $R^{52}$ for each radical have the meaning of one line in Table A in analogy to respectively $R^{41a}$, $R^{51a}$.

Analog to the above listed Table A, further examples of suitable radicals A are the radicals of the formulae A2 numbered A2b576 to A2b639 wherein Z is N—$CH_2CF_3$ and $R^{42}$, $R^{52}$ for each radical have the meaning of one line in Table A in analogy to respectively $R^{41a}$, $R^{51a}$.

A further embodiment of the invention relates to the methods and uses of compounds of the formulae I and II, to their salts, wherein A is a radical A3. Amongst these, preference is given to compounds of the formula I, wherein $X^1$, $R^1$, $R^2$ and $R^3$ are as defined above and in particular have one of the preferred meanings.

In the methods and uses of compounds of the formulae I and II, wherein A is a radical A3a, $R^{43a}$ is preferably selected from hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are as defined above and which are preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. In particular, $R^{43a}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl, and more preferably from $CH_3$, $CH_2CH_3$, $CHCF_2$, $CF_3$, Cl, Br.

In the methods and uses of compounds of the formulae I and II, wherein A is a radical A3a, $R^{53a}$ is preferably selected from the group as recited hereunder for the radical $R^{53}$.

A further embodiment of the invention relates to the methods and uses of compounds of the formulae I and II, to their salts, wherein A is a radical A3. Amongst these, preference is given to compounds of the formula I, wherein $X^1$, $R^1$, $R^2$ and $R^3$ are as defined above and in particular have one of the preferred meanings.

In the methods and uses of compounds of the formulae I and II, wherein A is a radical A3, $R^{43}$ is preferably selected from hydrogen, halogen, CN, $C_1$-$C_4$-alkyl, $C_1$-$C_4$-haloalkyl, $C_3$-$C_{10}$-cycloalkyl, $C_3$-$C_{10}$-halocycloalkyl and phenyl which may be unsubstituted or may carry 1, 2, 3, 4 or 5 identical or different substituents $R^x$ which are as defined above and which are preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. In particular, $R^{43}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl, and more preferably from and most preferably from $CH_3$, $CH_2CH_3$, $CHCF_2$, $CF_3$, Cl, Br.

In the methods and uses of compounds of the formulae I and II, wherein A is a radical A3 or A3a, $R^{53}$ or $R^{53a}$ is preferably selected from the group consisting of hydrogen, halogen, $C_1$-$C_{10}$-alkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl, phenoxy-methyl, 5- or 6-membered hetaryl, 5- or 6-membered hetarylmethyl wherein the (hetero)aromatic ring of the 5 last mentioned radicals may be unsubstituted or may carry 1, 2, 3, 4 or 5 identical or different substituents $R^x$ which are as defined above and preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{53}$ is selected from the group consisting of hydrogen, halogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl and $C_1$-$C_4$-alkoxy-$C_1$-$C_{10}$-alkyl. Most preferably $R^{53}$ is hydrogen, halogen, $C_1$-$C_4$-alkyl or $C_1$-$C_4$-haloalkyl, in particular methyl, ethyl, n-propyl, isopropyl, difluoromethyl, trifluoromethyl or 2,2,2-trifluoroethyl, and more preferably from $CH_3$, $CH_2CH_3$, $CHCF_2$, $CF_3$, Cl, Br.

In the methods and uses of compounds of the formulae I and II, wherein A is a radical A2, $R^{63}$ is preferably selected from the group consisting of $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_1$-$C_4$-alkoxy-$C_1$-$C_{10}$-alkyl, phenyl, benzyl and phenoxymethyl wherein the aromatic ring of the 3 last mentioned radicals may be unsubstituted or may carry 1, 2, 3, 4 or 5 identical or different substituents $R^x$ which is as defined above and more preferably selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl, and $C_1$-$C_4$-haloalkylsulfonyl. More preferably $R^{63}$ is $C_1$-$C_4$-alkyl or $C_1$-$C_4$-haloalkyl, in particular methyl, ethyl, n-propyl, isopropyl, Butyl, iso-butyl, sec-butyl, difluoromethyl, trifluoromethyl, 2-fluoroethyl, 2,2-difluoroethyl and 2,2,2-trifluoroethyl. In particular, more preferably are the methods and uses of compounds of the formulae I, wherein A is a radical A1, and $R^{63}$ is more preferably selected from hydrogen, methyl, ethyl, propyl, butyl, iso-butyl, sec-butyl, 2,2,2-trifluoroethyl.

Examples of such radicals of formula A3a or A3 are hereunder listed:

Analog to the above listed Table A, further examples of suitable radicals A are the radicals of the formulae A3a numbered A3a1 to A3a63 wherein Z is O and $R^{43a}$, $R^{53a}$ for each radical have the meaning of one line in Table A in analogy to respectively $R^{41a}$, $R^{51a}$.

Analog to the above listed Table A, further examples of suitable radicals A are the radicals of the formulae A3a numbered A3a64 to A3a127 wherein Z is S and $R^{43a}$, $R^{53a}$ for each radical have the meaning of one line in Table A in analogy to respectively $R^{41a}$, $R^{51a}$.

Analog to the above listed Table A, further examples of suitable radicals A are the radicals of the formulae A3 numbered A3b1 to A3b63 wherein Z is O and $R^{43}$, $R^{53}$ for each radical have the meaning of one line in Table A.

Analog to the above listed Table A, further examples of suitable radicals A are the radicals of the formulae A3 numbered A3b64 to A3b127 wherein Z is S and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b128 to A3b191 wherein Z is NH and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b192 to A3b255 wherein Z is $NCH_3$ and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b256 to A3b319 wherein Z is N-Et and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b320 to A3b383 wherein Z is N—Pr and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b384 to A3b447 wherein Z is N-Bu and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b448 to A3b511 wherein Z is N-iBu and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b4512 to A3b575 wherein Z is N-sBu and $R^{43}$, $R^{53}$ for each radical have the meaning of one line in Table A in analogy to respectively $R^{41a}$, $R^{51a}$.

Analog to the above listed Table A, further examples of suitable radicals A are the radicals of the formulae A3 numbered A3b575 to A3b639 wherein Z is N—$CH_2CF_3$ and $R^{43}$, $R^{53}$ for each radical have the meaning of one line in Table A in analogy to respectively $R^{41a}$, $R^{51a}$.

Apart from that, $X^3$ is preferably a lone pair. Compounds of the formulae I or II, wherein $X^3$ is O are also referred to as N-oxides of compounds I or II.

Apart from that, the variables Y, $R^a$, $R^b$, $R^c$, $R^d$, $R^e$, $R^f$, $R^g$, $R^h$, $R^x$ and $R^y$, independently of each other, preferably have one of the following meanings:

Y is preferably O;

$R^a$, $R^b$, $R^c$ are independently of each other selected from hydrogen, $C_1$-$C_4$-alkyl and $C_1$-$C_4$-haloalkyl;

$R^d$ is selected from $C_1$-$C_4$-alkyl and $C_1$-$C_4$-haloalkyl;

$R^e$, $R^f$ are independently of each other selected from hydrogen, $C_1$-$C_4$-alkyl, or $R^e$ and $R^f$ together with the nitrogen atom to which they are bound form a 5- or 6-membered, saturated heterocycle, which may carry a further heteroatom being selected from O, S and N as a ring member atom, e.g. pyrrolidin-1-yl, piperidin-1-yl, morpholin-4-yl, piperazin-1-yl or 4-methylpiperazin-1-yl;

$R^e$, $R^h$, $R^i$ are independently of each other selected from hydrogen and $C_1$-$C_4$-alkyl;

$R^x$ is selected from the group consisting of halogen, cyano, nitro, $C_1$-$C_4$-alkyl, $C_1$-$C_4$-alkoxy, $C_1$-$C_4$-haloalkoxy, $C_1$-$C_4$-alkylsulfonyl and $C_1$-$C_4$-haloalkylsulfonyl;

$R^y$ is selected from $C_1$-$C_4$-alkoxy, $C_3$-$C_6$-cycloalkyl and phenyl.

A very preferred embodiment of the invention relates to the methods and uses of compounds of the formula I and to their salts, wherein $X^1$ is O and $X^3$ is a lone pair. These compounds are hereinafter also referred to as compounds Ia.

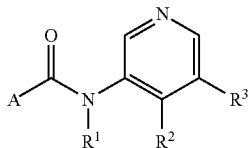

In formula Ia, the variables A, $R^1$, $R^2$ and $R^3$ are as defined herein. Amongst the compounds of the formula Ia, preference is given to those compounds, wherein A is a radical A1a or A1, e.g. a radical, selected from the 5-membered heterocyclic radicals numbered A1a1 to A1.a78. Amongst the compounds of the formula Ia, preference is given to those compounds, wherein at least one of the radicals $R^1$, $R^2$ and $R^3$, preferably at least two of the radicals $R^1$, $R^2$ and $R^3$, and more preferably all of the radicals $R^1$, $R^2$ and $R^3$ have one of the preferred meanings.

A particular preferred embodiment relates to the methods and uses of compounds of the formula Ia and to their salts, wherein A is a radical A1a, as defined herein, in particular a radical A1, wherein $R^{41a}$, $R^{51a}$ have the preferred meanings, in particular a radical selected from the radicals A1a64 to A1.78;

$R^1$ has the meaning as defined in each example of the Tables 1 to 72 hereunder listed;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment of methods and uses of such compounds are the compounds given in the following tables 1 to 72.

Table 1: Compounds of the formula Ia and their salts, wherein $R^1$, $R^2$ and $R^3$ are hydrogen and wherein A is selected from the radicals A1a1 to A1a78.

Table 2: Compounds of the formula Ia and their salts, wherein $R^1$ is $CH_3$, $R^2$ and $R^3$ are hydrogen and wherein A is selected from the radicals A1a1 to A1a78.

Table 3: Compounds of the formula Ia and their salts, wherein $R^1$ is $CH_2CH_3$, $R^2$ and $R^3$ are hydrogen and wherein A is selected from the radicals A1a1 to A1a78.

Table 4: Compounds of the formula Ia and their salts, wherein $R^1$ is propyl, $R^2$ and $R^3$ are hydrogen and wherein A is selected from the radicals A1a1 to A1a78.

Table 5: Compounds of the formula Ia and their salts, wherein $R^1$ is iso-propyl, $R^2$ and $R^3$ are hydrogen and wherein A is selected from the radicals A1a1 to A1a78.

Table 6: Compounds of the formula Ia and their salts, wherein $R^1$ is butyl, $R^2$ and $R^3$ are hydrogen and wherein A is selected from the radicals A1a1 to A1a78.

Table 7: Compounds of the formula Ia and their salts, wherein $R^1$ is iso-butyl, $R^2$ and $R^3$ are hydrogen and wherein A is selected from the radicals A1a1 to A1a78.

Table 8: Compounds of the formula Ia and their salts, wherein $R^1$ is tert-butyl, $R^2$ and $R^3$ are hydrogen and wherein A is selected from the radicals A1a1 to A1a78.

Table 9: Compounds of the formula Ia and their salts, wherein $R^1$ is $CH_2C(CH)_3$, $R^2$ and $R^3$ are hydrogen and wherein A is selected from the radicals A1a1 to A1a78.

Table 10: Compounds of the formula Ia and their salts, wherein $R^1$ is $CH_2=CHCCl_2$, $R^2$ and $R^3$ are hydrogen and wherein A is selected from the radicals A1a1 to A1a78.

Table 11: Compounds of the formula Ia and their salts, wherein $R^1$ is $CH_2CH=CBr_2$, $R^2$ and $R^3$ are hydrogen and wherein A is selected from the radicals A1a1 to A1a78.

Table 12: Compounds of the formula Ia and their salts, wherein $R^1$ is $CH_2CH_2Cl$, $R^2$ and $R^3$ are hydrogen and wherein A is selected from the radicals A1a1 to A1a78.

Table 13: Compounds of the formula Ia and their salts, wherein $R^1$ is $CH_2CH_2F$, $R^2$ and $R^3$ are hydrogen and wherein A is selected from the radicals A1a1 to A1a78.

Table 14: Compounds of the formula Ia and their salts, wherein $R^1$ is $CH_2CH_2Br$, $R^2$ and $R^3$ are hydrogen and wherein A is selected from the radicals A1a1 to A1a78.

Table 15: Compounds of the formula Ia and their salts, wherein $R^1$ is $CH_2CHF_2$, $R^2$ and $R^3$ are hydrogen and wherein A is selected from the radicals A1a1 to A1a78.

Table 16: Compounds of the formula Ia and their salts, wherein $R^1$ is $CH_2CHBr_2$, $R^2$ and $R^3$ are hydrogen and wherein A is selected from the radicals A1a1 to A1a78.

Table 17: Compounds of the formula Ia and their salts, wherein $R^1$ is $CH_2CHCl_2$, $R^2$ and $R^3$ are hydrogen and wherein A is selected from the radicals A1a1 to A1a78.

Table 18: Compounds of the formula Ia and their salts, wherein $R^1$ is $CH_2CF_3$, $R^2$ and $R^3$ are hydrogen and wherein A is selected from the radicals A1a1 to A1a78.

Table 19: Compounds of the formula Ia and their salts, wherein $R^1$ is $CH_2CN$, $R^2$ and $R^3$ are hydrogen and wherein A is selected from the radicals A1a1 to A1a78.

Table 20: Compounds of the formula Ia and their salts, wherein $R^1$ is $CH_2OCH_3$, $R^2$ and $R^3$ are hydrogen and wherein A is selected from the radicals A1a1 to A1a78.

Table 21: Compounds of the formula Ia and their salts, wherein $R^1$ is $CH_2OCH_2CH_3$, $R^2$ and $R^3$ are hydrogen and wherein A is selected from the radicals A1a1 to A1a78.

Table 22: Compounds of the formula Ia and their salts, wherein $R^1$ is $CH_2CH_2CN$, $R^2$ and $R^3$ are hydrogen and wherein A is selected from the radicals A1a1 to A1a78.

Table 23: Compounds of the formula Ia and their salts, wherein $R^1$ is $CH_2CHCN_2$, $R^2$ and $R^3$ are hydrogen and wherein A is selected from the radicals A1a1 to A1a78.

Table 24: Compounds of the formula Ia and their salts, wherein $R^1$ is $CH_2CH_2OCH_3$, $R^2$ and $R^3$ are hydrogen and wherein A is selected from the radicals A1a1 to A1a78.

Table 25: Compounds of the formula Ia and their salts, wherein $R^1$ is $CH_2CH_2OCH_2CH_3$, $R^2$ and $R^3$ are hydrogen and wherein A is selected from the radicals A1a1 to A1a78.

Table 26: Compounds of the formula Ia and their salts, wherein $R^1$ is ethylcyclopropane, $R^2$ and $R^3$ are hydrogen and wherein A is selected from the radicals A1a1 to A1a78.

Table 27: Compounds of the formula Ia and their salts, wherein $R^1$ is ethylcyclobutane, $R^2$ and $R^3$ are hydrogen and wherein A is selected from the radicals A1a1 to A1a78.

Table 28: Compounds of the formula Ia and their salts, wherein $R^1$ is 2-methyloxetane, $R^2$ and $R^3$ are hydrogen and wherein A is selected from the radicals A1a1 to A1a79.

Table 29: Compounds of the formula Ia and their salts, wherein $R^1$ is 3-ethyloxetane, $R^2$ and $R^3$ are hydrogen and wherein A is selected from the radicals A1a1 to A1a78.

Table 30: Compounds of the formula Ia and their salts, wherein $R^1$ is 3-methylthietane, $R^2$ and $R^3$ are hydrogen and wherein A is selected from the radicals A1a1 to A1a78.

Table 31: Compounds of the formula Ia and their salts, wherein $R^1$ is 3-methylthietane-1,1-dioxide, $R^2$ and $R^3$ are hydrogen and wherein A is selected from the radicals A1a1 to A1a78.

Table 32: Compounds of the formula Ia and their salts, wherein R¹ is ethylcyclopentane, R² and R³ are hydrogen and wherein A is selected from the radicals A1a1 to A1a78.

Table 33: Compounds of the formula Ia and their salts, wherein R¹ is 2-ethyltetrahydrofuran, R² and R³ are hydrogen and wherein A is selected from the radicals A1a1 to A1a78.

Table 34: Compounds of the formula Ia and their salts, wherein R¹ is 3-ethyltetrahydrofuran, R² and R³ are hydrogen and wherein A is selected from the radicals A1a1 to A1a78.

Table 35: Compounds of the formula Ia and their salts, wherein R¹ is methylcyclopropane, R² and R³ are hydrogen and wherein A is selected from the radicals A1a1 to A1a78.

Table 36: Compounds of the formula Ia and their salts, wherein R¹ is ethylcyclobutane, R² and R³ are hydrogen and wherein A is selected from the radicals A1a1 to A1a78.

Table 37: Compounds of the formula Ia and their salts, wherein R¹ is 2-methyloxetane, R² and R³ are hydrogen and wherein A is selected from the radicals A1a1 to A1a78.

Table 38: Compounds of the formula Ia and their salts, wherein R¹ is 3-methyloxetane, R² and R³ are hydrogen and wherein A is selected from the radicals A1a1 to A1a78.

Table 39: Compounds of the formula Ia and their salts, wherein R¹ is 3-methylthietane, R² and R³ are hydrogen and wherein A is selected from the radicals A1a1 to A1a78.

Table 40: Compounds of the formula Ia and their salts, wherein R¹ is 3-thietane-1,1-dioxide, R² and R³ are hydrogen and wherein A is selected from the radicals A1a1 to A1a78.

Table 41: Compounds of the formula Ia and their salts, wherein R¹ is cyclopentane, R² and R³ are hydrogen and wherein A is selected from the radicals A1a1 to A1a78.

Table 42: Compounds of the formula Ia and their salts, wherein R¹ is 2-methyltetrahydrofuran, R² and R³ are hydrogen and wherein A is selected from the radicals A1a1 to A1a78.

Table 43: Compounds of the formula Ia and their salts, wherein R¹ is tetrahydrofuran, R² and R³ are hydrogen and wherein A is selected from the radicals A1a1 to A1a78.

Table 44: Compounds of the formula Ia and their salts, wherein R¹ is toluene, R² and R³ are hydrogen and wherein A is selected from the radicals A1a1 to A1a78.

Table 45: Compounds of the formula Ia and their salts, wherein R¹ is 2-methylfuran, R² and R³ are hydrogen and wherein A is selected from the radicals A1a1 to A1a78.

Table 46: Compounds of the formula Ia and their salts, wherein R¹ is 3-methylfuran, R² and R³ are hydrogen and wherein A is selected from the radicals A1a1 to A1a78.

Table 47: Compounds of the formula Ia and their salts, wherein R¹ is 2-ethylthiophene, R² and R³ are hydrogen and wherein A is selected from the radicals A1a1 to A1a78.

Table 48: Compounds of the formula Ia and their salts, wherein R¹ is 3-methylthiophene, R² and R³ are hydrogen and wherein A is selected from the radicals A1a1A1a1 to A1a78.

Table 49: Compounds of the formula Ia and their salts, wherein R¹ is 5-ethylisothiazole, R² and R³ are hydrogen and wherein A is selected from the radicals A1a1 to A1a78.

Table 50: Compounds of the formula Ia and their salts, wherein R¹ is 4-ethylisothiazole, R² and R³ are hydrogen and wherein A is selected from the radicals A1a1 to A1a78.

Table 51: Compounds of the formula Ia and their salts, wherein R¹ is 3-methylisothiazole, R² and R³ are hydrogen and wherein A is selected from the radicals A1a1 to A1a78.

Table 52: Compounds of the formula Ia and their salts, wherein R¹ is 3-methylisoxazole, R² and R³ are hydrogen and wherein A is selected from the radicals A1a1 to A1a78.

Table 53: Compounds of the formula Ia and their salts, wherein R¹ is 5-methyloxazole, R² and R³ are hydrogen and wherein A is selected from the radicals A1a1 to A1a78.

Table 54: Compounds of the formula Ia and their salts, wherein R¹ is 2-ethyloxazole, R² and R³ are hydrogen and wherein A is selected from the radicals A1a1 to A1a78.

Table 55: Compounds of the formula Ia and their salts, wherein R¹ is 5-ethylthiazole, R² and R³ are hydrogen and wherein A is selected from the radicals A1a1 to A1a78.

Table 56: Compounds of the formula Ia and their salts, wherein R¹ is 2-ethylthiazole, R² and R³ are hydrogen and wherein A is selected from the radicals A1a1 to A1a78.

Table 57: Compounds of the formula Ia and their salts, wherein R¹ is 5-methyl-1H-pyrazole, R² and R³ are hydrogen and wherein A is selected from the radicals A1a1 to A1a78.

Table 58: Compounds of the formula Ia and their salts, wherein R¹ is 3-methyl-1H-pyrazole, R² and W are hydrogen and wherein A is selected from the radicals A1a1 to A1a78.

Table 59: Compounds of the formula Ia and their salts, wherein R¹ is 4-ethyl-1-methyl-1-H-pyrazole, R² and R³ are hydrogen and wherein A is selected from the radicals A1a1 to A1a78.

Table 60: Compounds of the formula Ia and their salts, wherein R¹ is 5-ethyl-1-methyl-1-H-pyrazole, R² and R³ are hydrogen and wherein A is selected from the radicals A1a1 to A1a78.

Table 61: Compounds of the formula Ia and their salts, wherein R¹ is 3-ethyl-1-methyl-1-H-pyrazole, R² and R³ are hydrogen and wherein A is selected from the radicals A1a1 to A1a78.

Table 62: Compounds of the formula Ia and their salts, wherein R¹ is 5-methyl-1H-imidazole, R² and R³ are hydrogen and wherein A is selected from the radicals A1a1 to A1a78.

Table 63: Compounds of the formula Ia and their salts, wherein R¹ is 4-ethyl-1H-imidazole, R² and R³ are hydrogen and wherein A is selected from the radicals A1a1 to A1a78.

Table 64: Compounds of the formula Ia and their salts, wherein R¹ is 3-CH₃—C₆H₄, R² and R³ are hydrogen and wherein A is selected from the radicals A1a1 to A1a78.

Table 65: Compounds of the formula Ia and their salts, wherein R¹ is 2-methyl-1H-imidazole, R² and R³ are hydrogen and wherein A is selected from the radicals A1a1 to A1a78.

Table 66: Compounds of the formula Ia and their salts, wherein R¹ is 5-ethyl-1-methyl-1-H-imidazole, R² and R³ are hydrogen and wherein A is selected from the radicals A1a1 to A1a78.

Table 67: Compounds of the formula Ia and their salts, wherein R¹ is 2-ethyl-1-methyl-1-H-imidazole, R² and R³ are hydrogen and wherein A is selected from the radicals A1a1 to A1a78.

Table 68: Compounds of the formula Ia and their salts, wherein R¹ is 1,4-dimethyl-1H-imidazole, R² and R³ are hydrogen and wherein A is selected from the radicals A1a1 to A1a78.

Table 69: Compounds of the formula Ia and their salts, wherein R¹ is 2-methyl-4,5-dihydrooxazole, R² and R³ are hydrogen and wherein A is selected from the radicals A1a1 to A1a78.

Table 70: Compounds of the formula Ia and their salts, wherein $R^1$ is 2-ethyl-4,5-dihydrothiazole, $R^2$ and $R^3$ are hydrogen and wherein A is selected from the radicals A1a1 to A1a78.

Table 71: Compounds of the formula Ia and their salts, wherein $R^1$ is 2-ethyl-4,5-dihydro-1H-imidazole, $R^2$ and $R^3$ are hydrogen and wherein A is selected from the radicals A1a1 to A1a78.

Table 72: Compounds of the formula Ia and their salts, wherein $R^1$ is 2-ethyl-1-methyl-4,5-dihydro-1H-imidazole, $R^2$ and $R^3$ are hydrogen and wherein A is selected from the radicals A1a1 to A1a78.

A further preferred embodiment relates to the methods and uses of compounds of the formula Ia and to their salts, wherein A is a radical A1, as defined herein, in particular a radical A1, wherein $R^{41}$, $R^{51}$ have the preferred meanings, in particular a radical A selected from the radicals A1b1 to A1b639;

$R^1$ has the meaning as defined in each example of the Tables 1 to 72;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment of methods and uses of such compounds are the compounds given in the following tables 73 to 145.

Tables 73 to 145: Compounds of the formula Ia and the salts and N-oxides thereof, wherein $R^2$ and $R^3$ are hydrogen, A is selected from the radicals A1b1 to A1b639 and wherein $R^1$ is as defined in tables 1 to 72.

A further preferred embodiment relates to the methods and uses of compounds of the formula Ia and to their salts, wherein A is a radical A2, as defined herein, in particular a radical A2, wherein $R^{42}$, $R^{52}$ have the preferred meanings, in particular a radical A selected from the radicals A2b1 to A2b639;

$R^1$ has the meaning as defined in each example of the Tables 1 to 72;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment of methods and uses of such compounds are the compounds given in the following tables 146 to 218.

Tables 146 to 218: Compounds of the formula Ia and the salts and N-oxides thereof, wherein $R^2$ and $R^3$ are hydrogen, A is selected from the radicals A2b1 to A2b639 and wherein $R^1$ is as defined in tables 1 to 72.

A further preferred embodiment relates to the methods and uses of compounds of the formula Ia and to their salts, wherein A is a radical A3, as defined herein, in particular a radical A3, wherein $R^{43}$, $R^{53}$ have the preferred meanings, in particular a radical A selected from the radicals A3b1 to A3b639;

$R^1$ has the meaning as defined in each example of the Tables 1 to 72;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment of methods and uses of such compounds are the compounds given in the following tables 219 to 291.

Tables 219 to 291: Compounds of the formula Ia and the salts and N-oxides thereof, wherein $R^2$ and $R^3$ are hydrogen, A is selected from the radicals A3b1 to A3b639 and wherein $R^1$ is as defined in tables 1 to 72.

A further preferred embodiment relates to the methods and uses of compounds of the formula Ia and to their salts, wherein A is a radical A2a, as defined herein, in particular a radical A2a, wherein $R^{42a}$, $R^{52a}$ have the preferred meanings, in particular a radical A selected from the radicals A2a1 to A2a127;

$R^1$ has the meaning as defined in each example of the Tables 1 to 72;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment of methods and uses of such compounds are the compounds given in the following tables 292 to 364.

Tables 292 to 364: Compounds of the formula Ia and the salts and N-oxides thereof, wherein $R^2$ and $R^3$ are hydrogen, A is selected from the radicals A2a1 to A2a127 and wherein $R^1$ is as defined in tables 1 to 72.

A further preferred embodiment relates to the methods and uses of compounds of the formula Ia and to their salts, wherein A is a radical A3a, as defined herein, in particular a radical A3a, wherein $R^{43a}$, $R^{53a}$ have the preferred meanings, in particular a radical A selected from the radicals A3a1 to A3a127;

$R^1$ has the meaning as defined in each example of the Tables 1 to 72;

$R^2$ is selected from hydrogen, methyl, difluoromethyl, trifluoromethyl, methoxy, difluoromethoxy and trifluoromethoxy; and $R^3$ is selected from hydrogen, methyl, difluoromethyl, trifluoromethyl, methoxy, difluoromethoxy and trifluoromethoxy; and wherein preferably one or both radicals $R^2$ and $R^3$ are hydrogen.

Examples of compounds of this particular preferred embodiment of methods and uses of such compounds are the compounds given in the following tables 365 to 437.

Tables 365 to 437: Compounds of the formula Ia and the salts and N-oxides thereof, wherein $R^2$ and $R^3$ are hydrogen, A is selected from the radicals A3a1 to A3a127 and wherein $R^1$ is as defined in tables 1 to 72.

The compounds of the formulae I or II can be prepared by the standard methods of organic chemistry, e.g. by the methods described hereinafter or in the working examples:

The compounds of the formula Ia, wherein $X^1$ is O and $X^3$ is a lone pair, can be prepared e.g. according to the method depicted in scheme 1 by reacting activated oxazole or thiazole or imidazole or isoxazole or isothiazole carboxylic acid derivative IIa with a 3-aminopyridine compound III (see e.g. Houben-Weyl: "Methoden der organ. Chemie" [Methods of Organic Chemistry], Georg-Thieme-Verlag, Stuttgart, New York 1985, Volume E5, pp. 941-1045). Activated oxazole or thiazole or imidazole or isoxazole or isothiazole carboxylic acid derivatives IIa are, for example, acyl halides, activated esters, anhydrides, acyl azides, wherein X is for example chlorine, fluorine, bromine, para-nitrophenoxy, pentafluorophenoxy, N-hydroxysuccinimides, hydroxybenzotriazol-1-yl. In scheme 1, the radicals A, $R^1$, $R^2$ and $R^3$ have the meanings mentioned above and in particular the meanings mentioned as being preferred.

Scheme 1:

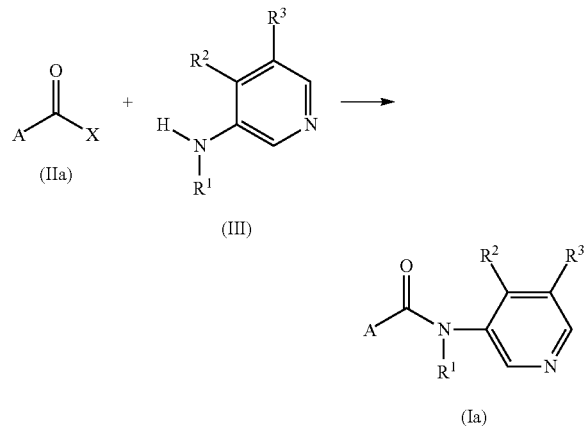

The active compounds of the formula Ia, wherein $X^1$ is O and $X^3$ is a lone pair, can also be prepared, for example, by reacting the oxazole or thiazole or imidazole or isoxazole or isothiazole carboxylic acid IV with a 3-aminopyridine compound III in the presence of a coupling agent according to scheme 2. In scheme 2, the radicals A, $R^1$, $R^2$ and $R^3$ have the meanings given above and in particular the meanings given as being preferred.

Scheme 2:

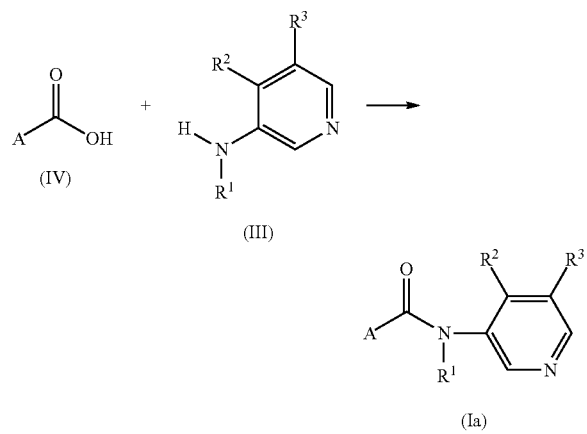

Suitable coupling agents are, for example:
coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide;
coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun. 1972, 942];
coupling agents based on phosphonium salts, for example (benzotriazol-1-yloxy)tris(dimethylamino)phosphonium hexafluorophosphate [B. Castro, J. R. Domoy, G. Evin, C. Selve, Tetrahedron Lett. 1975, 14, 1219], (benzotriazol-1-yl-oxy)tripyrrolidinophosphonium hexafluorophosphate [J. Coste et al., Tetrahedron Lett. 1990, 31, 205];
coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N,N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647];
coupling agents which form acid chlorides, for example bis-(2-oxo-oxazolidinyl)phosphinic chloride [J. Diago-Mesequer, Synthesis 1980, 547].

Compounds Ia where $X^1$ is O, $X_3$ is a lone pair and $R^1$ is different from hydrogen can also be prepared by alkylating the corresponding amides as shown in Scheme 3 (in which $R^1$ is hydrogen and which can be obtained according to scheme 1 or 2) using suitable alkylating agents in the presence of bases.

Scheme 3:

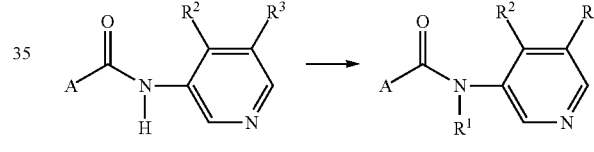

The oxazole or thiazole or imidazole or isoxazole or isothiazole carboxylic acids IV and their activated derivatives IIa as well as 3-aminopyridine compound III are known in the art or are commercially available or can be prepared by methods known from the literature.

Compounds of the formula I, wherein $X^1$ is different from oxygen, can be prepared from the compounds Ia by standard methods:

Compounds of the formula I, wherein $X^1$ is S, can be prepared e.g. by reacting a compound 1a with 2,4-bis(4-methoxyphenyl)-1,3,2,4-dithiadiphosphetane-2,4-disulfide or phosphorus pentasulfide according to the method described by M. Jesberger et al. in Synthesis 2003, 1929.

Compounds of the formula I, wherein $X^1$ is $NR^{1a}$, can be prepared e.g. by reacting a compound Ia with by reacting a compound Ia with 2,4-bis(4-methoxyphenyl)-1,3,2,4-dithiadiphosphetane-2,4-disulfide to obtain the corresponding thioamide (compound I, wherein $X^1$ is S) which is then reacted with an appropriate amine according to the method described by V. Glushkov et al. in Pharmaceutical Chemistry Journal 2005, 39(10), 533-536.

Compounds of the formula II, wherein $X^2$=$SR^{2a}$, can be prepared by alkylation of the corresponding thioamide (compound I, wherein $X^1$ is S) by reaction with an alkylating agent according to the method described by V. Glushkov et al. in Pharmaceutical Chemistry Journal 2005, 39(10), 533-536. In a similar manner, compounds I, wherein $X^2$ is $OR^{2a}$ or $NR^{2b}R^{2c}$ can be obtained. Compounds of the formula II, wherein $X^2$=$SOR^{2a}$ or $SO_2R^{2a}$ can be obtained by oxidation of compounds II with $X^2$=$SR^{2a}$.

Compounds of the formulae I and II, wherein $X^3$ is O, can be prepared by oxidation of compounds I, wherein $X^3$ is a lone pair, according to standard methods of preparing pyridine N-oxides, e.g. by the method described C. Botteghi et al. in Journal of Organometallic Chemistry 1989, 370, 17-31.

As a rule, the compounds of the formulae I or II can be prepared by the methods described above. If individual compounds cannot be prepared via the above-described routes, they can be prepared by derivatization of other compounds I or II or by customary modifications of the synthesis routes described. For example, in individual cases, certain compounds I or II can advantageously be prepared from other compounds I or II by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration. Ronan please check all the preparation part.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formulae (I) or (II) or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formulae (I) or (II) or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating such invertebrate pests, which comprises such an amount of at least one compound of the general formulae I or II or at least one agriculturally useful salt or N-oxide thereof and at least one inert liquid and/or solid agronomically acceptable carrier that has a pesticidal action and, if desired, at least one surfactant.

Such a composition may contain a single active compound of the formulae I or II or a salt or N-oxide thereof or a mixture of several active compounds I or II or their salts according to the present invention. The composition according to the present invention may comprise an individual isomer or mixtures of isomers as well as individual tautomers or mixtures of tautomers.

The compounds of the formulae I or II and the pestidicidal compositions comprising them are effective agents for controlling arthropod pests and nematodes. Invertebrate pests controlled by the compounds of formulae I or II include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysornya hominivorax, Chrysomya macellaria, Contarinia sorghicola, Cordylobia anthropophaga, Culex pipiens, Dacus cucurbitae, Dacus*

*oleae, Dasineura brassicae, Fannia canicularis, Gasterophilus intestinalis, Glossina morsitans, Haematobia irritans, Haplodiplosis equestris, Hylernyia platura, Hypoderma lineata, Liriornyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocarnpa testudinea, Monomorium pharaonis, Solenopsis germinata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptornyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascatonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* siphonatera, e.g. *Xenopsylla cheopsis, Ceratophyllus* spp.

The compositions and compounds of formulae I or II are useful for the control of nematodes, especially plant parasitic nematodes such as root knot nematodes, *Meloidogyne hapla, Meloidogyne incognita, Meloidogyne javanica,* and other *Meloidogyne* species;

cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formulae I or II are used for controlling insects or arachnids, in particular insects of the orders Lepidoptera, Coleoptera, Thysanoptera and Homoptera and arachnids of the order Acarina. The compounds of the formulae I or II according to the present invention are particularly useful for controlling insects of the order Thysanoptera and Homoptera.

The compounds of formula formulae I or II or the pesticidal compositions comprising them may be used to protect growing plants and crops from attack or infestation by invertebrate pests, especially insects, acaridae or arachnids by contacting the plant/crop with a pesticidally effective amount of compounds of formulae I or II. The term "crop" refers both to growing and harvested crops.

The compounds of formulae I or II can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, anti-foaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95 by weight, preferably from 0.1 to 90 by weight, of the active compound(s). In this case, the active compound(s) are employed in a purity of from 90 to 100 by weight, preferably 95 to 100 by weight (according to NMR spectrum).

For seed treatment purposes, respective formulations can be diluted 2- to 10-fold leading to concentrations in the ready to use preparations of 0.01 to 60 by weight active compound by weight, preferably 0.1 to 40 by weight.

The compounds of formulae I or II can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and if appropriate, solvent or oil, and such concentrates are suitable for dilution with water.

The active compound concentrations in the ready-to-use preparations can be varied within relatively wide ranges. In general, they are from 0.0001 to 10, preferably from 0.01 to 1 per weight.

The active compound(s) may also be used successfully in the ultra-low-volume process (ULV), it being possible to apply formulations comprising over 95 by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetting agents or other auxiliaries are added. The active compound(s) dissolves upon dilution with water, whereby a formulation with 10 (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20 (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15 (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25 (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound(s), whereby a formulation with 20 (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50 (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75 (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20 (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5 (w/w) of active compound(s)

J) Granules (GR, FG, GG, MG)

0.5 parts by weight of the active compound(s) is ground finely and associated with 95.5 parts by weight of carriers, whereby a formulation with 0.5 (w/w) of active compound(s) is obtained. Current methods are extrusion, spray-drying or the fluidized bed. This gives granules to be applied undiluted for foliar use K) ULV Solutions (UL)

10 parts by weight of the active compound(s) are dissolved in 90 parts by weight of an organic solvent, for example xylene. This gives a product having 10 (w/w) of active compound(s), which is applied undiluted for foliar use.

The compounds of formulae I or II are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter In a preferred embodiment a FS formulation is used for seed treatment. Typically, a FS formulation may comprise 1 to 800 g/l of active ingredient, 1 to 200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formulae I or II for seed treatment comprise from 0.5 to 80 wt of the active ingredient, from 0.05 to 5 wt of a wetting agent, from 0.5 to 15 wt of a dispersing agent, from 0.1 to 5 wt of a thickener, from 5 to 20 wt of an anti-freeze agent, from 0.1 to 2 wt of an anti-foam agent, from 1 to 20 wt of a pigment and/or a dye, from 0 to 15 wt of a sticker/adhesion agent, from 0 to 75 wt of a filler/vehicle, and from 0.01 to 1 wt of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formulae I or II are effective through both contact (via soil, glass, wall, bed net, carpet, plant parts or animal parts), and ingestion (bait, or plant part).

For use against ants, termites, wasps, flies, mosquitoes, crickets, or cockroaches, compounds of formulae I or II are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formulae I or II as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, am-photeric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formulae I or II and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formulae I or II and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formulae I and II or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formulae I or II into contact with each other, and "seed dressing" to methods of seed treatment which provide the seeds with an amount of the compounds of formulae I or II, i.e. which generate a seed comprising the compound of formulae I or II. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formulae I or II or the enantiomers or veterinarily acceptable salts thereof are in particular also suitable for being used for combating parasites in and on animals.

A further object of the present invention is therefore to provide new methods for controlling parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formulae I or II or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of compounds of formulae I or II or the enantiomers or veterinarily acceptable salts thereof and an acceptable carrier or a composition comprising it.

The present invention also provides a non-therapeutic method for treating, controlling, preventing and protecting animals against infestation and infection by parasites, which comprises applying to a locus-P a parasiticidally effective amount of a compound of formulae I or II or the enantiomers or veterinarily acceptable salts thereof and an acceptable carrier or a composition comprising it.

The invention also provides a process for the preparation of a composition for treating, controlling, preventing or protecting animals against infestation or infection by parasites which comprises including a parasiticidally effective amount of a compound of formulae I or II or the enantiomers or veterinarily acceptable salts thereof and an acceptable carrier or a composition comprising it.

The invention relates further to the use of compounds of formula I for treating, controlling, preventing or protecting animals against infestation or infection by parasites. The invention relates also to the use of a compound of formulae I or II or the enantiomers or veterinarily acceptable salts thereof and an acceptable carrier or a composition comprising it for the manufacture of a medicament for the therapeutic treatment of animals against infections or infestations by parasites.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly, it has been found that compounds of formulae I or II are suitable for combating endo- and ectoparasites in and on animals.

Compounds of formulae I or II or the enantiomers or veterinarily acceptable salts thereof and compositions comprising them are preferably used for controlling and preventing infestations and infections animals including, warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formulae I or II or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formulae I or II or the enantiomers or veterinarily acceptable salts thereof and compositions comprising them are suitable for systemic and/or non-systemic control of ecto- and/or endoparasites. They are active against all or some stages of development.

The compounds of formulae I or II are especially useful for combating ectoparasites.

The compounds of formulae I or II are especially useful for combating parasites of the following orders and species, respectively:

fleas (Siphonaptera), e.g. *Ctenocephalides felis*, *Ctenocephalides canis*, *Xenopsylla cheopis*, *Pulex irritans*, *Tunga penetrans*, and *Nosopsyllus fasciatus*, cockroaches (Blattaria-Blattodea), e.g. *Blattella germanica*, *Blattella asahinae*, *Periplaneta americana*, *Periplaneta japonica*, *Periplaneta brunnea*, *Periplaneta fuligginosa*, *Periplaneta australasiae*, and *Blatta orientalis*, flies, mosquitoes (Diptera), e.g. *Aedes aegypti*, *Aedes albopictus*, *Aedes vexans*, *Anastrepha ludens*, *Anopheles maculipennis*, *Anopheles crucians*, *Anopheles albimanus*, *Anopheles gambiae*, *Anopheles freeborni*, *Anopheles leucosphyrus*, *Anopheles minimus*, *Anopheles quadrimaculatus*, *Calliphora vicina*, *Chrysornya bezziana*, *Chrysomya hominivorax*, *Chrysomya macellaria*, *Chrysops discalis*, *Chrysops silacea*, *Chrysops atlanticus*, *Cochliomyia hominivorax*, *Cordylobia anthropophaga*, *Culicoides furens*, *Culex pipiens*, *Culex nigripalpus*, *Culex quinquefasciatus*, *Culex tarsalis*, *Culiseta inornata*, *Culiseta melanura*, *Dermatobia hominis*, *Fannia canicularis*, *Gasterophilus intestinalis*, *Glossina morsitans*, *Glossina palpalis*, *Glossina fuscipes*, *Glossina tachinoides*, *Haematobia irritans*, *Haplodiplosis equestris*, *Hippelates* spp., *Hypoderma lineata*, *Leptoconops torrens*, *Lucilia caprina*, *Lucilia cuprina*, *Lucilia sericata*, *Lycoria pectoralis*, *Mansonia* spp., *Musca domestica*, *Muscina stabulans*, *Oestrus ovis*, *Phlebotomus argentipes*, *Psorophora columbiae*, *Psorophora discolor*, *Prosimulium mixtum*, *Sarcophaga haemorrhoidalis*, *Sarcophaga* sp., *Simulium vittatum*, *Stomoxys calcitrans*, *Tabanus bovinus*, *Tabanus atratus*, *Tabanus lineola*, and *Tabanus similis*, lice (Phthiraptera), e.g. *Pediculus humanus capitis*, *Pediculus humanus corporis*, *Pthirus pubis*, *Haematopinus eurysternus*, *Haematopinus suis*, *Linognathus vituli*, *Bovicola bovis*, *Menopon gallinae*, *Menacanthus stramineus* and *Solenopotes capillatus*, ticks and parasitic mites (Parasitiformes): ticks (Ixodida), e.g. *Ixodes scapularis*, *Ixodes holocyclus*, *Ixodes pacificus*, *Rhiphicephalus sanguineus*, *Dermacentor andersoni*, *Dermacentor variabilis*, *Amblyomma americanum*, *Ambryomma maculatum*, *Ornithodorus hermsi*, *Ornithodorus turicata* and parasitic mites (Mesostigmata), e.g. *Ornithonyssus bacoti* and *Dermanyssus gallinae*, actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius*, *Cimex hemipterus*, *Reduvius senilis*, *Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm), Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Varnpirolepis* spp., *Moniezia* spp., *Anoplocephala* spp., *Sirometra* spp., *Anoplocephala* spp., and *Hymenolepis* spp.

The compounds of formulae I or II and compositions containing them are particularly useful for the control of pests from the orders Diptera, Siphonaptera and Ixodida.

Moreover, the use of the compounds of formulae I or II and compositions containing them for combating mosquitoes is especially preferred.

The use of the compounds of formulae I or II and compositions containing them for combating flies is a further preferred embodiment of the present invention.

Furthermore, the use of the compounds of formulae I or II and compositions containing them for combating fleas is especially preferred.

The use of the compounds of formula formulae I or II and compositions containing them for combating ticks is a further preferred embodiment of the present invention.

The compounds of formulae I or II and compositions containing them also are especially useful for combating endoparasites (roundworms nematoda, thorny headed worms and planarians).

The compounds of formulae I or II and compositions containing them can be effective through both contact (via soil, glass, wall, bed net carpet, blankets or animal parts) and ingestion (e.g. baits).

The present invention relates to the therapeutic and the non-therapeutic use of compounds of formulae I or II and compositions containing them for controlling and/or combating parasites in and/or on animals.

The compounds of formulae I or II and compositions containing them may be used to protect the animals from attack or infestation by parasites by contacting them with a parasitically effective amount of compounds of formulae I or II and compositions containing them. As such, "contacting" includes both direct contact (applying the pesticidal mixtures/compositions directly on the parasite, which may include an indirect contact at it's locus-P, and optionally also administrating the pesticidal mixtures/composition directly on the animal) and indirect contact (applying the compounds/compositions to the locus of the parasite). The contact of the parasite through application to its locus is an example of a non-therapeutic use of compounds of formula I.

"Locus-P" as defined above means the habitat, food supply, breeding ground, area, material or environment in which a parasite is growing or may grow outside of the animal. The compounds of the invention can also be applied preventively to places at which occurrence of the pests or parasites is expected.

Administration can be carried out both prophylactically and therapeutically.

Administration of the active compounds is carried out directly or in the form of suitable preparations, orally, topically/dermally or parenterally.

For oral administration to warm-blooded animals, the compounds of formula I or II may be formulated as animal feeds, animal feed premixes, animal feed concentrates, pills, solutions, pastes, suspensions, drenches, gels, tablets, boluses and capsules. In addition, the compounds of formulae I or II may be administered to the animals in their drinking water. For oral administration, the dosage form chosen should provide the animal with 0.01 mg/kg to 100 mg/kg of animal body weight per day of the formulae I or II compound, preferably with 0.5 mg/kg to 100 mg/kg of animal body weight per day. Alternatively, the compounds of formulae I or II may be administered to animals parenterally, for example, by intraruminal, intramuscular, intravenous or subcutaneous injection. The compounds of formulae I or II may be dispersed or dissolved in a physiologically acceptable carrier for subcutaneous injection. Alternatively, the compounds of formulae I or II may be formulated into an implant for subcutaneous administration. In addition the compounds of formulae I or II may be transdermally administered to animals. For parenteral administration, the dosage form chosen should provide the animal with 0.01 mg/kg to 100 mg/kg of animal body weight per day of the compounds of formulae I or II.

The compounds of formulae I or II may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5 000 ppm and preferably 1 ppm to 3 000 ppm of the compounds of formulae I or II. In addition, the compounds of formulae I or II may be formulated as ear tags for animals, particularly quadrupeds such as cattle and sheep.

Suitable Preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, N-alkylpyrrolidones such as N-Methylpyrrolidone, N-butylpyrrolidone or N-octylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable Emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity. For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95 of the compound of formulae I or II.

Generally, it is favorable to apply the compounds of formulae I or II in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formulae I or II against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formulae I or II are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formulae I or II in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formulae I or II. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and super-phosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formulae I or II or the compositions comprising them in the use form as pesticides with other pesticides frequently results in a broader pesticidal spectrum of action.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cyproprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbannoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]amide (M22.4) and 4-[5-(3,5-Dichlorophenyl)-5-trifluoromethyl-4,5-dihydro-isoxazol-3-yl]-N-[(methoxyimino)methyl]-2-methylbenzamide (M22.5);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropylethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoropropyl)malononitrile ($CF_2H-CF_2-CF_2-CF_2-CH_2-C(CN)_2-CH_2-CH_2-CF_3$) (M24.1) and 2-(2,2,3,3,4,4,5,5-octafluoropentyl)-2-(3,3,4,4,4-pentafluorobutyl)-malonodinitrile ($CF_2H-CF_2-CF_2-CF_2-CH_2-C(CN)_2-CH_2-CH_2-CF_2-CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:
4-{[(6-Bromopyrid-3-yl)methyl](2-fluoroethyl)amino}furan-2(5H)-on (M26.1),
4-{[(6-Fluoropyrid-3-yl)methyl](2,2-difluoroethyl)amino}furan-2(5H)-on (M26.2),
4-{[(2-Chloro1,3-thiazolo-5-yl)methyl](2-fluoroethyl)amino}furan-2(5H)-on (M26.3),
4-{[(6-Chloropyrid-3-yl)methyl](2-fluoroethyl)amino}furan-2(5H)-on (M26.4),
4-{[(6-Chloropyrid-3-yl)methyl](2,2-difluoroethyl)amino}furan-2(5H)-on (M26.5),
4-{[(6-Chloro-5-fluoropyrid-3-yl)methyl](methyl)amino}furan-2(5H)-on (M26.6),
4-{[(5,6-Dichloropyrid-3-yl)methyl](2-fluoroethyl)amino}furan-2(5H)-on (M26.7),
4-{[(6-Chloro-5-fluoropyrid-3-yl)methyl](cyclopropyl)amino}furan-2(5H)-on (M26.8),
4-{[(6-Chloropyrid-3-yl)methyl](cyclopropyl)amino}furan-2(5H)-on (M26.9) and 4-{[(6-Chloropyrid-3-yl)methyl](methyl)amino}furan-2 (5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclopropanecarboxamide-2-(2,6-dichloro-α,α,α-trifluoro-p-tolyl)hydrazone or N—R"-2,2-di(R''')propionamide-2-(2,6-dichloro-α, α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a, 12b-decahydro-12-hydroxy-4,6a,12b-trimethyl-11-oxo-9-(3-pyridinyl)-2H,11H-naphtho[2,1-b]pyrano[3,4-e]pyran-3, 6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 14th Edition, British Crop Protection Council (2006) among other publications.

Lepimectin is known from Agro Project, PJB Publications Ltd, November 2004. Benclothiaz and its preparation have been described in EP-A1454621. Methidathion and Paraoxon and their preparation have been described in Farm Chemicals Handbook, Volume 88, Meister Publishing Company, 2001. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Cyantraniliprole has been described in WO 01/70671, WO 04/067528 and WO 05/118552. The anthranilamides M23.1 to M23.6 have been described in WO 2008/72743 and WO 200872783, those M23.7 to M23.12 in WO2007/043677. The phthalamide M 21.1 is known from WO 2007/101540. Cyflumetofen and its preparation have been described in WO 04/080180. The aminoquinazolinone compound pyrifluquinazon has been described in EP A 109 7932. Sulfoximine sulfoxaflor has been described in WO 2006/060029 and WO 2007/149134. The alkynylether compound M27.1 is described e.g. in JP 2006131529. Organic sulfur compounds have been described in WO 2007060839. The isoxazoline compounds M 22.1 to M 22.5 have been described in e.g. WO2005/085216, WO 2007/079162 and WO 2007/026965. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

Fungicidal mixing partners are in particular those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, enestroburin, fluoxastrobin, kresoxim-methyl, me-tominostrobin, orysastrobin, picoxystrobin, pyraclostrobin, pyribencarb or trifloxystrobin, sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the compound(s) of formulae I or II or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formulae I or II. As such the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formulae I or II and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I and II are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formulae I and II can also be applied preventively to places at which occurrence of the pests is expected.

The compounds of formulae I or II may also be used to protect growing plants from attack or infestation by pests by contacting the plant with a pesticidally effective amount of compounds of formula I or II. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001 by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 5 g to 600 g per hectare, more desirably from 10 g to 300 g per hectare.

In the treatment of seed, the application rates of the active ingredients are generally from 0.1 g to 10 kg per 100 kg of seed, preferably from 1 g to 1 kg per 100 kg of seed, in particular from 1 g to 250 g per 100 kg of seed, in particular from 50 g to 150 g per 100 kg of seed.

The present invention is now illustrated in further detail by the following examples but is not limited to them.

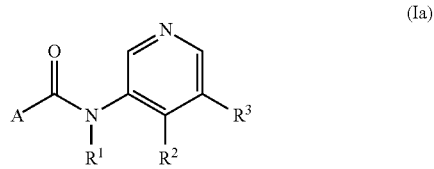

(Ia)

I. PREPARATION EXAMPLES

The procedures described in the following preparation examples were used to prepare further compounds of formulae (Ia) by appropriate modification of the starting material. The resulting compounds, together with physical data, are listed below.

Products were characterized by HPLC (High Performance Liquid Chromatography Mass Spectrometry). HPLC was carried out using an analytic RP-18 column (Chromolith Speed ROD from Merck KgaA, Germany) which was operated at 40° C. Acetonitrile with 0.1 by volume of a trifluoroacetic acid/water mixture and 0.1 by volume of trifluoroacetic acid served as mobile phase; flow rate: 1.8 ml/min and injection volume: 2 µl.

Example 15

3-Cyclopropyl-isoxazole-4-carboxylic acid pyridin-3-ylamide

3-Cyclopropyl-isoxazole-4-carboxylic acid 5.6 g (31 mmol) of 3-Cyclopropyl-isoxazole-4-carboxylic acid ethyl ester were slowly added to a solution of 6.1 g (93 mmol, 85% purity) of potassium hydroxide in ethanol/water (1:3, 100 ml) at 0° C. The reaction mixture was stirred at room temperature for 16 h, diluted with water, acidified (pH=2) with 20% aqueous HCl and extracted with dichloromethane. The combined organic layers were dried over sodium sulfate, filtered and the solvent was removed to yield 4.7 g (94%, 95% purity) of the title compound which did not need further purification.

3-Cyclopropyl-isoxazole-4-carboxylic acid pyridin-3-ylamide 400 mg (2.6 mmol) of 3-cyclopropyl-isoxazole-4-carboxylic acid were suspended in 10 mL of toluene and one drop of dimethylformamide was added to the mixture. 0.24 mL of thionylchloride (3.3 mmol) were added at room temperature and the reaction mixture was stirred at 65° C. for two hours. After removal of the solvent, toluene was added and the evaporation was repeated. The obtained residue was then dissolved in 5 mL of dichloromethane and the solution was added dropwise to a solution containing 246 mg pyridin-3-ylamine (2.6 mmol) and 0.45 ml triethyl amine (3.3 mmol) in 5 ml dichloromethane. The mixture was stirred at room temperature for 16 h and the solvent was removed under vacuum. The residue was purified by flash column chromatography (silica, gradient elution cyclohexane→ethyl acetate→methanol) and the solvent was removed under vacuum to give 436 mg (69%, 95% purity) of the title compound as a brown solid.

Example 2

5-Br-thiazole-4-carboxylic acid pyridin-3-yl-amide 150 mg (0.43 mmol) of 5-bromo-thiazole-4-carboxylic acid and 81.4 mg (0.87 mmol) of pyridin-3-yl-amine were dissolved in 6 ml dimethyl formamide. 0.09 mL (0.65 mmol) of triethyl amine followed by 225 mg (0.43 mmol) of 1H-benzotriazol-1-yloxytri-pyrrolidinophosphonium hexafluorophosphate (PyBOP) were added and the reaction mixture was stirred at room temperature for 16 h. Brine was added and the reaction mixture was extracted two times with dichloromethane. The combined organic layers were dried over sodium sulfate, filtered and the solvent was removed under reduced pressure. The obtained residue was purified by flash column chromatography (silica, gradient elution cyclohexane→ethyl acetate→methanol) to give 90 mg (66%, 90% purity) of the title compound.

Compounds of formula (Ia) prepared according to the above mentioned method together with their physico-chemical data are compiled below. $R^1$ and A in each case have the meanings given in the corresponding line and $R^2$ and $R^3$ in each case are hydrogen. The corresponding physico-chemical data r.t. =HPLC retention time is given.

| Example | $R^1$ | A | physico-chemical data: r.t. [min] |
|---|---|---|---|
| 1 | H | 5-Br-thiazol-4-yl | 1.494 |
| 2 | Me | 2-(4-Cl-phenyl)-oxazol-4-yl | 2.414 |
| 3 | Me | 3-Me-isoxazol-4-yl | 1.115 |
| 4 | H | 3-Me-isoxazol-4-yl | 1.272 |
| 5 | H | 4-Me-thiazol-5-yl | 1.199 |
| 6 | Me | 3-Et-isoxazol-4-yl | 1.434 |
| 7 | Me | 4-Me-thiazol-5-yl | 1.123 |
| 8 | H | 3-Et-isoxazol-4-yl | 1.562 |
| 9 | H | 3-Cyclopropyl-isoxazol-4-yl | 1.612 |
| 10 | Me | 3-Cyclopropyl-isoxazol-4-yl | 1.490 |
| 11 | H | 3-Methyl-5-phenyl-isoxazol-4-yl | 2.034 |
| 12 | H | 1H-Imidazol-2-yl | 0.610 |
| 13 | H | 1H-Imidazol-4-yl | 0.563 |
| 14 | H | 2-Methyl-1H-imidazol-4-yl | 0.548 |
| 15 | H | 3-Cyclopropyl-isoxazol-5-yl | 1.611 |
| 16 | H | 2-Methyl-5-(trifluoromethyl)-oxazol-4-yl | 1.806 |
| 17 | H | 2-Methyl-4-(trifluormethyl)-thiazol-5-yl | 1.643 |
| 18 | H | 5-Methyl-2-(4-trifluoromethylphenyl)-3H-imidazol-4-yl | 2.323 |
| 19 | H | 2,5-Dimethyl-oxazol-4-yl | 1.496 |
| 20 | H | 5-Methyl-oxazol-4-yl | 1.288 |
| 21 | H | 4-Methyl-oxazol-5-yl | 1.035 |
| 22 | H | Oxazol-5-yl | 0.886 |
| 23 | H | 2,4-Dimethyl-oxazol-5-yl | 1.255 |
| 24 | H | 2,4-Dimethyl-thiazol-5-yl | 1.348 |
| 25 | H | 2-Methyl-oxazol-4-yl | 1.577 |
| 26 | H | Isothiazol-5-yl | 1.166 |

II. EVALUATION OF PESTICIDAL ACTIVITY

II.1 Cotton Aphid (*Aphis gossypii*, Mixed Life Stages)
Method a)

The active compounds were formulated in 50:50 (vol:vol) acetone:water and 100 ppm Kinetica™ (from Helena Chemical Co.) surfactant.

Cotton plants at the cotyledon stage (one plant per pot) were infested by placing a heavily infested leaf from the main colony on top of each cotyledon. The aphids were allowed to transfer to the host plant overnight, and the leaf used to transfer the aphids was removed. The cotyledons were dipped in the test solution and allowed to dry. After 5 days, mortality counts were made.

In this test, the compounds 4, 5, 15, 17, 19, 20, 21, 22, 23, 24 and 25 respectively, at 300 ppm showed a mortality of at least 90% in comparison with untreated controls.
Method b)

The active compounds were formulated in cyclohexanone as a 10,000 ppm solution supplied in 1.3 ml ABgene® (from ABgene) tubes. These tubes were inserted into an automated electrostatic sprayer equipped with an atomizing nozzle and they served as stock solutions for which lower dilutions were made in 50% acetone:50% water (v/v). A nonionic surfactant (Kinetic® from Helena Chemical Co.) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 3, 5, 6, 7, 8, 9, 10 and 11 respectively, at 300 ppm showed a mortality of at least 75% in comparison with untreated controls.
II.2 Green Peach Aphid (*Myzus persicae*, Mixed Life Stages)
Method a)

The active compounds were formulated in 50:50 (vol:vol) acetone:water and 100 ppm Kinetica™ (from Helena Chemical Co.) surfactant.

Pepper plants in the $2^{nd}$ leaf-pair stage (variety 'California Wonder') were infested with approximately 40 laboratory-reared aphids by placing infested leaf sections on top of the test plants. The leaf sections were removed after 24 hr. The leaves of the intact plants were dipped into gradient solutions of the test compound and allowed to dry. Test plants were maintained under fluorescent light (24 hour photoperiod) at about 25° C. and 20-40% relative humidity. Aphid mortality on the treated plants, relative to mortality on check plants, was determined after 5 days.

In this test, compounds 4, 5, 15, 16, 17, 21, 22, 23, 24 and 25 respectively, at 300 ppm showed a mortality of at least 90% in comparison with untreated controls.
Method b)

The active compounds were formulated in cyclohexanone as a 10,000 ppm solution supplied in 1.3 ml ABgene® (from ABgene) tubes. These tubes were inserted into an automated electrostatic sprayer equipped with an atomizing nozzle and they served as stock solutions for which lower dilutions were made in 50 acetone:50% water (v/v). A nonionic surfactant (Kinetic®) (from Helena Chemical Co.) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle.

The plants were dried in the sprayer fume hood, removed, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 2, 3, 5, 6, 8, 9 and 10 respectively, at 300 ppm showed a mortality of at least 75% in comparison with untreated controls.

II.3 Cowpea Aphid (*Aphis craccivora*)

The active compounds were formulated in 50:50 (vol:vol) acetone:water. The test solution was prepared at the day of use.

Potted cowpea plants colonized with 100-150 aphids of various stages were sprayed after the pest population had been recorded. Population reduction was assessed after 24, 72, and 120 hours.

In this test, the compounds 3, 4, 5, 6, 8, 9, 10, 12, 13, 14, 15, 19, 20, 21, 22, 23, 24, 25 and 26 respectively, at 300 ppm showed a mortality of at least 90% in comparison with untreated controls.

II.4 Vetch Aphid (*Megoura viciae*)

The active compounds were formulated in 1:3 (vol:vol) DMSO:water with different concentrations of formulated compounds.

Bean leaf disks were placed into microtiterplates filled with 0.8 agar-agar and 2.5 ppm OPUS™ (from BASF SE, conazole). The leaf disks were sprayed with 2.5 µl of the test solution and 5 to 8 adult aphids were placed into the microtiterplates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds 4, 5, 9, 10, 13, 15, 17, 19, 20, 21, 23 and 24 respectively at a concentration of the test solution of 2500 mg/L showed a mortality of at least 90%.

II.5 Boll Weevil (*Anthonomus grandis*)

The compounds were formulated in 75:25 (vol:vol) water: DMSO.

For evaluating control of boll weevil (*Anthonormus grandis*) the test unit consisted of 24-well-microtiter plates containing an insect diet and 20-30 *A. grandis* eggs. Different concentrations of formulated compounds were sprayed onto the insect diet at 20 µl, using a custom built micro atomizer, at two replications. After application, the microtiter plates were incubated at 23±1° C. and 50±5% relative humidity for 5 days. Egg and larval mortality was then visually assessed.

In this test, the compounds 4, 5, 10, 14, 18 and 23 respectively at a concentration of the test solution of 2500 mg/L showed a mortality of at least 50%.

II.6 Activity Against Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications. After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds 4, 5, 9, 10, 15, 17, 20, 22, 23, 24 and 25 respectively, at 2500 ppm showed 100% mortality in comparison with untreated controls.

II.7 Activity Against Brown Planthopper (*Nilaparvata lugens*)

The active compounds were formulated as a 50:50 (vol:vol) acetone:water solution. Surfactant (Alkamuls EL 620) (Rhone-Poulenc) was added at the rate of 0.1% (vol/vol). Rice seedlings were cleaned and washed 24 h before spraying. Potted rice seedlings were sprayed with 5 ml test solution, air dried, placed in cages and inoculated with 10 adults. Treated rice plants were kept at 28-29° C. and relative humidity of 50-60% mortality was recorded after 72 hours.

In this test, compounds 1, 4 and 20 respectively at 500 ppm showed a mortality of at least 50% in comparison with untreated controls.

II.8 Activity in the Hydroponic Tests Against Green Peach Aphids (*Myzus persicae*)

Green pepper plants (*Capsicum annuum* L., variety 'California Wonder') are grown in the greenhouse from seed to the second true leaf stage (BBCH 12) in Scott's MetroMix® 360 (Sungro Horticulture) (1-2 plants per 2¼" square pot). Cotyledon leaves are removed and roots are rinsed in tap water until free of soil. The roots are kept moist under a layer of wet paper toweling until all plants have been prepared.

A 3400 ppm stock solution is prepared of each test compound using reagent grade acetone as the solvent. Subsequent dilutions of 100 and 10 ppm are prepared from this stock with final dilutions in deionized water in 100 ml amber glass bottles. One bare root plant is placed in each bottle using a foam plug section to centrally secure the stem in the bottleneck. The bare roots are fully-immersed in the test suspensions. Host plants are placed in a plant growth room under continuous GroLux® fluorescent lighting (40 W), for 24 hours at 25±2° C. and 20-40% RH.

After exposure of the bare roots to the test suspensions, pieces of pepper plants infested with green peach aphid (*Myzus persicae*) are placed on top of the test foliage. Insects are allowed to transfer from the host leaves to accomplish an infestation of 40-50 insects per plant. The assay is allowed to run for 3 days in the same growth chamber as used previously. Assessments include estimates of aphid population density reduction relative to the average density of aphids on the untreated control plants. Phytotoxic responses of the host plants are also recorded at this time.

In this test, compounds 3, 4, 8 and 10 respectively at 100 ppm showed a mortality of at, least 75% in comparison with untreated controls.

II.9 Activity in the Hydroponic Tests Against Cotton Aphids (*Aphis gossypii*)

Cotton plants (*Gossypium hirsutum*, variety 'Sure Grow 747') are grown in the greenhouse from seed to the second true leaf stage (BBCH 12) in Scott's Metro-Mix® 360 (Sungro Horticulture) (1-2 plants per 2¼" square pot). Cotyledon leaves are removed and roots are rinsed in tap water until free of soil. The roots are kept moist under a layer of wet paper toweling until all plants have been prepared.

A 3400 ppm stock solution is prepared of each test compound using reagent grade acetone as the solvent. Subsequent dilutions of 100 and 10 ppm are prepared from this stock with final dilutions in deionized water in 100 ml amber glass bottles. One bare root plant is placed in each bottle using a foam plug section to centrally secure the stem in the bottleneck. The bare roots are fully-immersed in the test suspensions. Host plants are placed in a plant growth room under continuous GroLux® fluorescent lighting (40 W), for 24 hours at 25±2° C. and 20-40% RH.

After exposure of the bare roots to the test suspensions, pieces of cotton plants infested with cotton aphids (*Aphis gossypii*) are placed on top of the test foliage. Insects are allowed to transfer from the host leaves to accomplish an infestation of 40-50 insects per plant. The assay is allowed to run for 3 days in the same growth chamber as used previously. Assessments include estimates of aphid population density reduction relative to the average density of aphids on the untreated control plants. Phytotoxic responses of the host plants are also recorded at this time.

In this test, compounds 3, 6, 8, 9 and 10 respectively at 100 ppm showed a mortality of at least 75% in comparison with untreated controls.

The invention claimed is:

1. A method for controlling and/or combating insects which method comprises treating the insects, their food supply, their habitat or their breeding ground or a plant, seed, soil, area, material or environment in which the insects are growing or may grow, or the materials, plants, seeds, soils, surfaces or spaces to be protected from insect attack or infestation with a pesticidal effective amount of a compound of formula (I), or a salt or an N-oxide thereof:

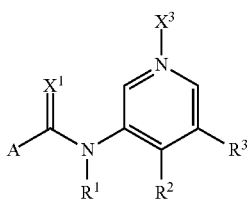
(I)

wherein
A is an isoxazole or isothiazole radical of formula A1a, A2a, or A3a

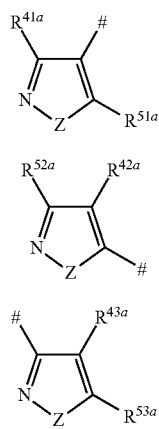

A1a

A2a

A3a denotes the bonding site to the remainder of formula (I)
$X^3$ is a lone pair or oxygen;
Z is O or S;
$R^1$ is hydrogen, $C_1$-$C_3$-alkyl or $C_1$-$C_4$-alkylene-CN;
$R^2$ is hydrogen, methyl, difluoromethyl, trifluoromethyl, methoxy, difluoromethoxy or trifluoromethoxy;
$R^3$ is hydrogen, methyl, difluoromethyl, trifluoromethyl, methoxy, difluoromethoxy or trifluoromethoxy;
$R^{41a}$, $R^{43a}$, $R^{52a}$, and $R^{53a}$ are independently selected from the group consisting of hydrogen, halogen, CN, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated, or may carry 1 or 2 identical or different substituents $R^y$ wherein
$R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_mR^d$, $S(O)_mNR^eR^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl wherein m is 0, 1 or 2 and $R^d$ $C_1$-$C_4$-alkyl or $C_1$-$C_4$-haloalkyl;
with the proviso that either $R^{41a}$ or $R^{51a}$ is H if Z is O;
$R^{42a}$ is selected from the group consisting of hydrogen, halogen, $NO_2$, $C_1$-$C_{10}$-alkyl, $C_3$-$C_{10}$-cycloalkyl, $C_5$-$C_{10}$-cycloalkenyl, $C_3$-$C_{10}$-cycloalkylmethyl, $C_2$-$C_{10}$-alkenyl, $C_2$-$C_{10}$-alkynyl, wherein the aliphatic or cyclic moieties in the 6 last mentioned radicals may be unsubstituted, may be partially or fully halogenated;
$X^1$ is O.

2. The method as claimed in claim 1, wherein the pesticidal compound is a compound of the formula (I), wherein $R^1$ is hydrogen, methyl or ethyl.

3. The method as claimed in claim 1, wherein in formula (I) A is a radical A1a, $R^{41a}$ and $R^{51a}$ are independently selected from the group consisting of hydrogen, halogen, $C_1$-$C_{10}$-alkyl, $C_3$-$C_{10}$-cycloalkyl, $C_2$-$C_{10}$-alkenyl and $C_2$-$C_{10}$-alkynyl, wherein the aliphatic or cyclic moieties in the 4 last mentioned radicals may be unsubstituted, may be partially or fully halogenated or may carry 1 or 2 identical or different substituents $R^y$ wherein
$R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_mR^d$, $S(O)_mNR^eR^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl wherein m is 0, 1 or 2 and $R^d$ $C_1$-$C_4$-alkyl or $C_1$-$C_4$-haloalkyl.

4. The method as claimed in claim 1, wherein the insects are of the order Homoptera.

* * * * *